US012582474B2

(12) United States Patent
Nakamura et al.

(10) Patent No.: US 12,582,474 B2
(45) Date of Patent: Mar. 24, 2026

(54) VISUALIZATION OF THREE-DIMENSIONAL IMAGE DATA ON TWO-DIMENSIONAL IMAGES

(71) Applicant: CANON U.S.A., INC., Melville, NY (US)

(72) Inventors: Hitoshi Nakamura, Boston, MA (US); Antonio Bonillas Vaca, Boston, MA (US)

(73) Assignee: Canon U.S.A., Inc., Melville, NY (US)

( * ) Notice: Subject to any disclaimer, the term of this patent is extended or adjusted under 35 U.S.C. 154(b) by 1057 days.

(21) Appl. No.: 17/237,668

(22) Filed: Apr. 22, 2021

(65) Prior Publication Data

US 2021/0330387 A1 Oct. 28, 2021

Related U.S. Application Data

(60) Provisional application No. 63/013,989, filed on Apr. 22, 2020.

(51) Int. Cl.
*A61B 34/10* (2016.01)
*A61B 34/20* (2016.01)
*A61B 90/00* (2016.01)

(52) U.S. Cl.
CPC .............. *A61B 34/10* (2016.02); *A61B 34/20* (2016.02); *A61B 90/37* (2016.02); *A61B 2034/107* (2016.02); *A61B 2034/2065* (2016.02); *A61B 2034/2068* (2016.02); *A61B 2090/363* (2016.02); *A61B 2090/367* (2016.02); *A61B 2090/372* (2016.02)

(58) Field of Classification Search
None
See application file for complete search history.

(56) References Cited

U.S. PATENT DOCUMENTS

| | | | |
|---|---|---|---|
| 9,222,966 B2 | 12/2015 | Amanuma | |
| 9,222,996 B2 | 12/2015 | Fujimoto et al. | |
| 9,269,141 B2 | 2/2016 | Wiemker et al. | |
| 9,710,146 B2 | 7/2017 | Tokunaga et al. | |
| 9,867,667 B2 | 1/2018 | Fujimoto et al. | |
| 9,867,673 B2 | 1/2018 | Onuma et al. | |
| 10,163,228 B2 | 12/2018 | Kim et al. | |
| 10,499,879 B2 | 12/2019 | Veronesi et al. | |
| 10,614,335 B2 | 4/2020 | Cohen-Solal et al. | |
| 2011/0007071 A1 | 1/2011 | Pfister | |
| 2011/0236868 A1 | 9/2011 | Bronstein et al. | |
| 2013/0106905 A1* | 5/2013 | Sunaga | A61B 5/055 345/619 |
| 2014/0027597 A1 | 1/2014 | Farris | |

(Continued)

FOREIGN PATENT DOCUMENTS

| | | |
|---|---|---|
| JP | 2003-10149 A | 1/2003 |
| JP | 2014-526946 A | 10/2014 |

(Continued)

*Primary Examiner* — Patricia J Park
(74) *Attorney, Agent, or Firm* — Canon U.S.A., Inc., IP Division

(57) ABSTRACT

The present disclosure relates generally to medical imaging and, more particularly to systems, methods, and devices for planning and carrying out minimally invasive procedures using external devices for needle guidance and the display and manipulation of the image set when planning and performing the procedure.

21 Claims, 15 Drawing Sheets

(56)                    References Cited

U.S. PATENT DOCUMENTS

| | | | |
|---|---|---|---|
| 2014/0229881 A1* | 8/2014 | Schadewaldt | G06T 19/00 |
| | | | 715/771 |
| 2015/0279061 A1 | 10/2015 | Kutsuna et al. | |
| 2015/0356245 A1 | 12/2015 | Kozuka et al. | |
| 2016/0007406 A1 | 1/2016 | Yi et al. | |
| 2017/0000058 A1 | 1/2017 | Huskowska et al. | |
| 2017/0003055 A1 | 1/2017 | De Luca | |
| 2017/0007162 A1 | 1/2017 | Choi et al. | |
| 2017/0017245 A1 | 1/2017 | Jovanovic | |
| 2017/0337336 A1 | 11/2017 | Weidner | |
| 2018/0344290 A1* | 12/2018 | Veronesi | A61B 8/466 |
| 2019/0000859 A1 | 1/2019 | Shi et al. | |
| 2019/0005687 A1 | 1/2019 | Weingarten et al. | |
| 2019/0008591 A1* | 1/2019 | Desai | G06T 7/0012 |
| 2019/0046232 A1 | 2/2019 | Tokuda et al. | |
| 2019/0151023 A1 | 5/2019 | Lu et al. | |
| 2019/0151026 A1 | 5/2019 | Lu et al. | |
| 2019/0282301 A1 | 9/2019 | Bonillas Vaca | |
| 2020/0030044 A1 | 1/2020 | Wang et al. | |
| 2020/0121287 A1 | 4/2020 | Nakamura | |
| 2020/0121392 A1 | 4/2020 | Daniels | |

FOREIGN PATENT DOCUMENTS

| | | | |
|---|---|---|---|
| WO | 2016-004007 A1 | 1/2016 | |
| WO | 2017/180643 A1 | 10/2017 | |
| WO | 2018/075671 A1 | 4/2018 | |
| WO | 2018175094 A1 | 9/2018 | |
| WO | 2019-074958 A1 | 4/2019 | |

* cited by examiner

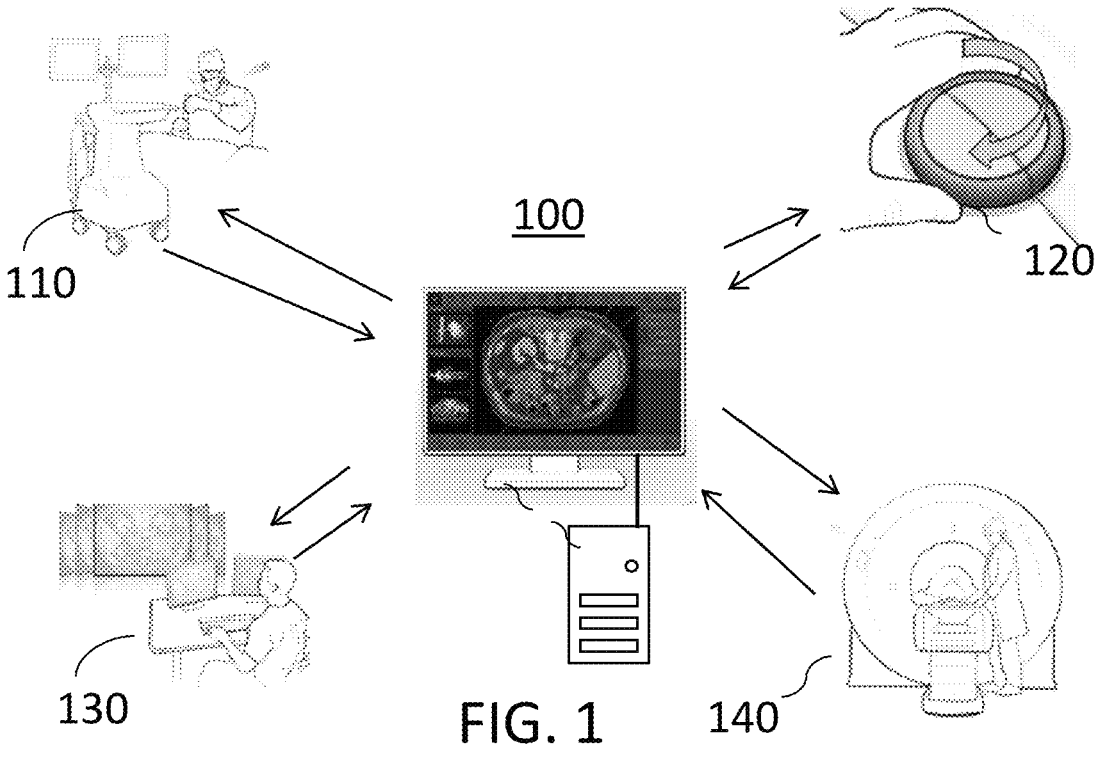
100
110
120
130
FIG. 1    140
100
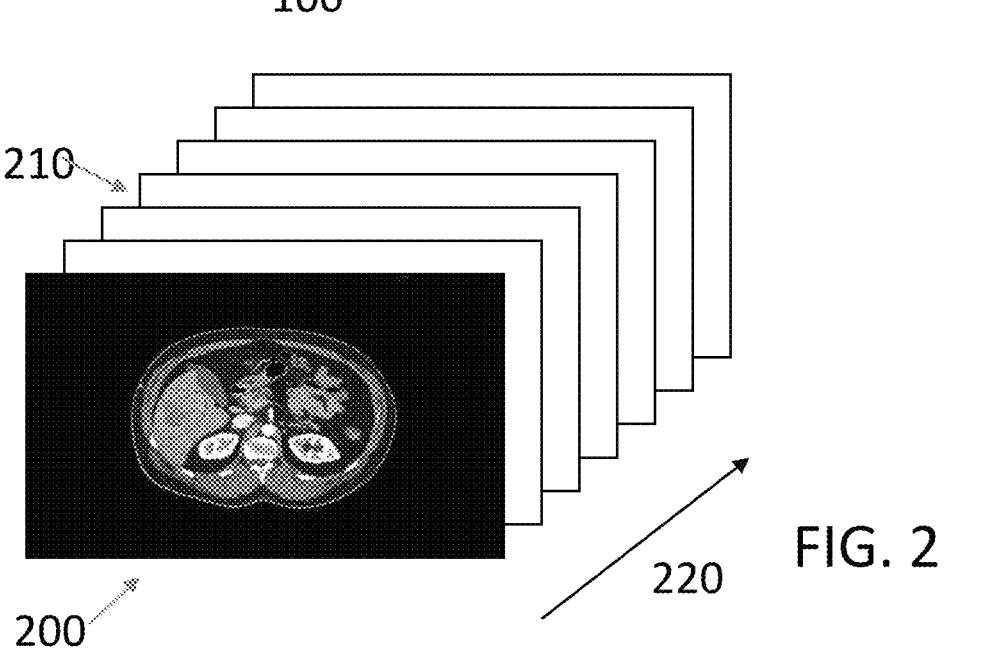
210
220    FIG. 2
200

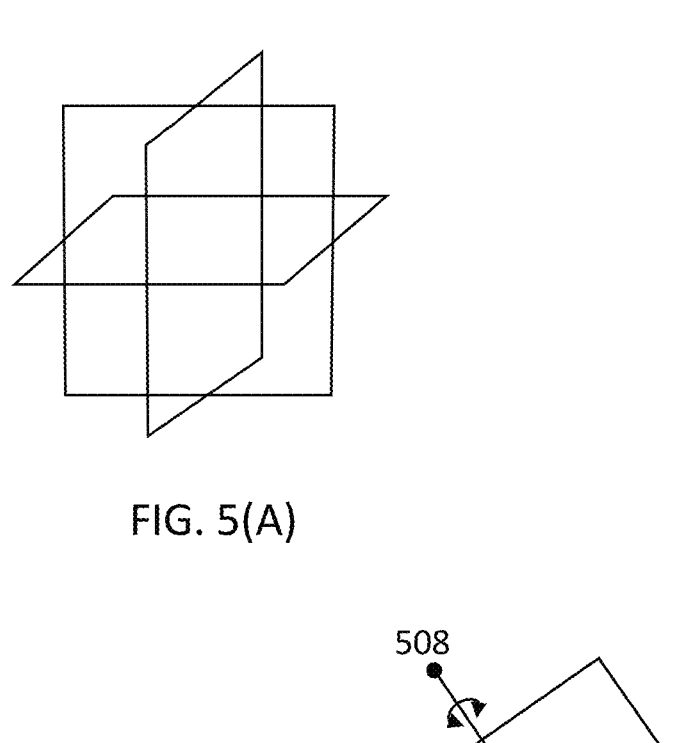
FIG. 5(A)
FIG. 5(B)
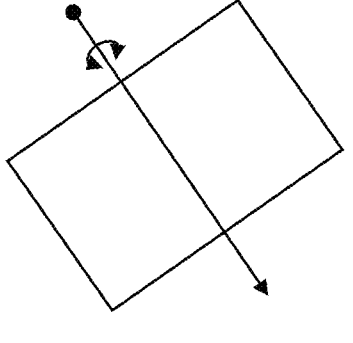
FIG. 5(C)
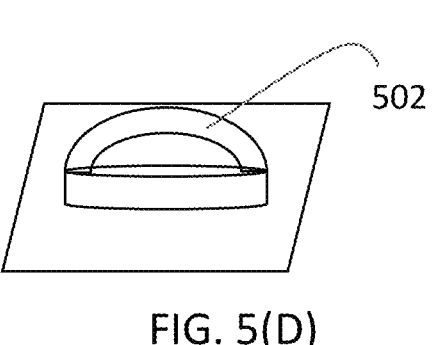
FIG. 5(D)
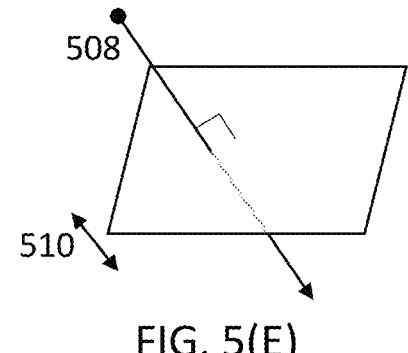
FIG. 5(E)
FIG. 5

(Axial view)  (Base view)  (Sagittal view)

(Axial view)  (Base view)  (Sagittal view)

VISUALIZATION OF THREE-DIMENSIONAL IMAGE DATA ON TWO-DIMENSIONAL IMAGES

CROSS-REFERENCE TO RELATED APPLICATION(S)

This application claims priority to U.S. Patent Application Ser. No. 63/013,989 filed Apr. 22, 2020, the entire disclosure of which is incorporated by reference herein in its entirety.

FIELD OF THE INVENTION

The present disclosure relates generally to medical imaging and, more particularly to systems, methods, and devices for planning and carrying out minimally invasive procedures using external devices for needle guidance.

BACKGROUND OF THE INVENTION

Minimally invasive medical procedures are becoming increasingly popular in the medical community due to shortened hospital stays and improved quality of life for the patient. For example, in the field of interventional oncology, percutaneous ablations are often preferred over surgical resection due to the minimally invasive nature of the procedure and thus shortened patient recovery period.

Medical images assist physicians in planning, performing, and post-operative analysis of minimally invasive and other procedures. Some imaging modalities that are useful include ultrasound imaging, computed tomography (CT), and magnetic resonance imaging (MRI). Medical images can also be used to assist in navigating various instruments relative to the patient while performing a procedure.

During planning, for minimally invasive image-guided needle interventions (biopsy, ablation therapy, etc.), a target lesion or anatomy is usually identified in medical images of modalities such CT, MRI, etc. An insertion point on the skin surface is also usually identified in the medical images to plan the needle trajectory. To aid in directing the needle along the planned trajectory a guidance device may be used, positioned on or near the patient skin. The device geometry plus the length of the needle will place constraints on the reachable area, so a mental picture is formed based on knowledge of the device, experience and measurements on the image data to determine whether the target is reachable from the chosen insertion point. During a procedure using a guidance device, the device is placed on the patient and new images are acquired, on which the device can be identified and registered to the image space. It can then be confirmed whether the target is reachable.

However, the medial images are generally scanned in a cross-section relative to the patient anatomy (e.g., the patient lies on the gantry within a CT or MRI bore) and the cross sectional images are obtained without reference to the relative location of the target lesion and the skin entry point. Thus, when viewing a two-dimensional image on the screen, it can be difficult to visualize and understand the relationship between the target lesion, the skin entry point, and any critical structures or other features that could affect the intervention.

Thus, in conventional systems, there is limited ability to plan, perform, and analyze the effectiveness of the procedure with sufficient simplicity, accuracy, no provision for simulating the device placement in the imaging software during planning for evaluating target reachability. Thus, before the guidance device is placed on the patient, imaged and registered to the image space, it is difficult to be certain that the target point is reachable from the chosen insertion point using the device. It is also difficult, when multiple different images are displayed simultaneously, how those images interconnect.

While U.S. Pat. No. 9,710,146; U.S. Pat. Pub. 2011/0007071 and others have provided systems and methods for image display control that supports a user in selecting an image of interested from among a three-dimensional data set, it does not allow for a simple and intuitive way of planning and carrying out minimally invasive procedures for needle guidance.

Thus, there is need for devises, systems, and methods to overcome the problems as discussed above.

SUMMARY OF THE INVENTION

Accordingly, it is a broad object of the present disclosure to provide devices, systems, and methods to allow a clinician to easily visualize 3D images on a 2D display to provide planning, performance, and evaluation techniques.

The present disclosure provides an image processing apparatus and a method of use for supporting a needle placement process, planning, or assessment comprising a processor that operates to: acquire a three-dimensional image set comprising a stack of two-dimensional image slices; cause a display to display a first image slice from the three-dimensional image set in a first image mode; cause the display to display, concurrent with the first image slice, a first indicator element associated with the first image mode; cause a display to display a second image slice from the three-dimensional image set in a second image mode; cause the display to display, concurrent with the first image slice, a second indicator element associated with the second image mode; wherein the first and second indicator elements each indicate: the location of the first and second two-dimensional image slice within the three-dimensional image set, respectively, and the location of the at least one region of interest and/or at least one target point.

The image processing apparatus and method for use as provided herein comprise a processor that operates to: acquire a three-dimensional image set comprising a stack of image slices; cause a display to display: (a) a first image slice from the three-dimensional image set in a first image mode and a first indicator element associated with the first image mode and containing a first marker that indicates location of at least one of the first image slice within the three-dimensional image set, an insertion point, a target point, or a region of interest; and (b) a second image slice from the three-dimensional image set in a second image mode and a second indicator element associated with the second image mode and containing a second marker that indicates at least one of the location of the second image slice within the three-dimensional image set, an insertion point, a target point, or a region of interest; wherein the processor further operates, based on a user selecting and moving the first marker or the second marker, to: (a) update the display of the first image slice to an updated first image slice in the first image mode, wherein the first marker indicates the location of the updated first image slice, the insertion point, the target point, or the region of interest; and (b) update the display of the second image slice to an updated second image slice in the second image mode, wherein the second marker indicates the location of the updated second image slice the insertion point, the target point, or the region of interest. If the user selecting and moving a marker and the resultant change of the selected visualized image would not correspond to a different visualized image in another of the imaging modes, then the updating the display of the second image slice would not result in a change to the displayed visualized image slice or marker.

Also provided are methods for visualizing, performing planning or treatment for a percutaneous probe treatment, by using the apparatus and/or processor as described herein. Other embodiments include a server storing an imaging application having instructions that, when executed by a processor, cause the server to perform the methods as described herein. Yet other embodiments include a non-transitory computer-readable storage medium storing an imaging application to cause an imaging server to perform the methods as described herein.

In some embodiments, the indicator bar as described in U.S. Patent Publication 2020/0121393 filed Oct. 2, 2019 as well as the apparatus and methods describe therein are combined with the invention as describe here. The entire disclosure of U.S. Patent Publication 2020/0121393 is incorporated by reference herein in its entirety. In one or more embodiments, the guidance devices as described in U.S. Pat. Nos. 9,222,996, 9,867,667, 9,867,673, 10,274,553, 10,285, 670, 10,251,670, 10,639,065, 10,420,626, 10,869,613, 10,695,087, WO2018/075671, each of which are incorporated by reference herein in their entirety may be used in conjunction with the planning, performance, and evaluation apparatuses and systems, and methods as described herein.

In accordance with one or more embodiments of the present disclosure, visualizing, planning, performance, and evaluation apparatuses and systems, and methods and storage mediums may operate to characterize and/or treat biological objects, such as, but not limited to, lesions, tumors, critical structures, etc.

In accordance with at least another aspect of the present disclosure, the planning, performance, and evaluation technique(s) systems and methods discussed herein may be employed to reduce the cost of at least one of manufacture and maintenance of planning, performance, and evaluation devices, systems and storage mediums by reducing or minimizing a number of components therein to cut down cost.

According to other aspects of the present disclosure, one or more additional devices, one or more systems, one or more methods and one or more storage mediums for planning, performance, and evaluation are discussed herein. Further features of the present disclosure will in part be understandable and will in part be apparent from the following description and with reference to the attached drawings.

BRIEF DESCRIPTION OF THE DRAWINGS

For the purposes of illustrating various aspects of the disclosure, wherein like numerals indicate like elements, there are shown in the drawings simplified forms that may be employed, it being understood, however, that the disclosure is not limited by or to the precise arrangements and instrumentalities shown. To assist those of ordinary skill in the relevant art in making and using the subject matter hereof, reference is made to the appended drawings and figures, wherein:

FIG. 1 is a schematic diagram showing an embodiment of a system for performing a needle placement in accordance with one or more aspects of the present disclosure.

FIG. 2 is schematic of multiple slice images in a CT scan.

FIGS. 5(A)-5(E) illustrate the orientation of the multiple different view modes that may be used in conjunction with the indicator element as described in several embodiments of the invention. FIG. 5(A) provides the orientations of the Multi Planer Reconstruction (MPR) view modes of axial, sagittal, and coronal view. FIG. 5(B) is the orientation of the arc view image mode. FIG. 5(C) is the orientation of the trajectory view. FIG. 5(D) is of the base view image mode FIG. 5(E) is of the flythrough image mode where the needle trajectory is shown as 508.

FIGS. 6(A), (B), (C) and (D) are sidebars for each side. FIG. 6(E) is a curved bar; FIG. 6(F) is a closed bar; FIGS. 6(G) and 6(H) are overlay lines; FIG. 6(I) is a 3D image to visualize angle; and FIG. 6(J) is an icon to visualize relative angle.

FIG. 9(A) is an illustration of an embodiment of the indicator element that is a closed bar indicator for a Trajectory image mode. FIG. 9(B) is an illustration of an embodiment of the indicator element that is a closed bar indicator for an Arc image mode.

FIG. 10(A) shows one linked view for each of axial, base, and sagittal views. FIG. 10(B) shows a second linked view of the three imaging modes where the visualized axial slice is different.

FIG. 11(A) is an exemplary embodiment with three imaging modes and three indicator bars. FIG. 11(B) contains three view modes in 3D space and three indicator bars.

DETAILED DESCRIPTION OF THE PRESENT INVENTION

Figure 3A:
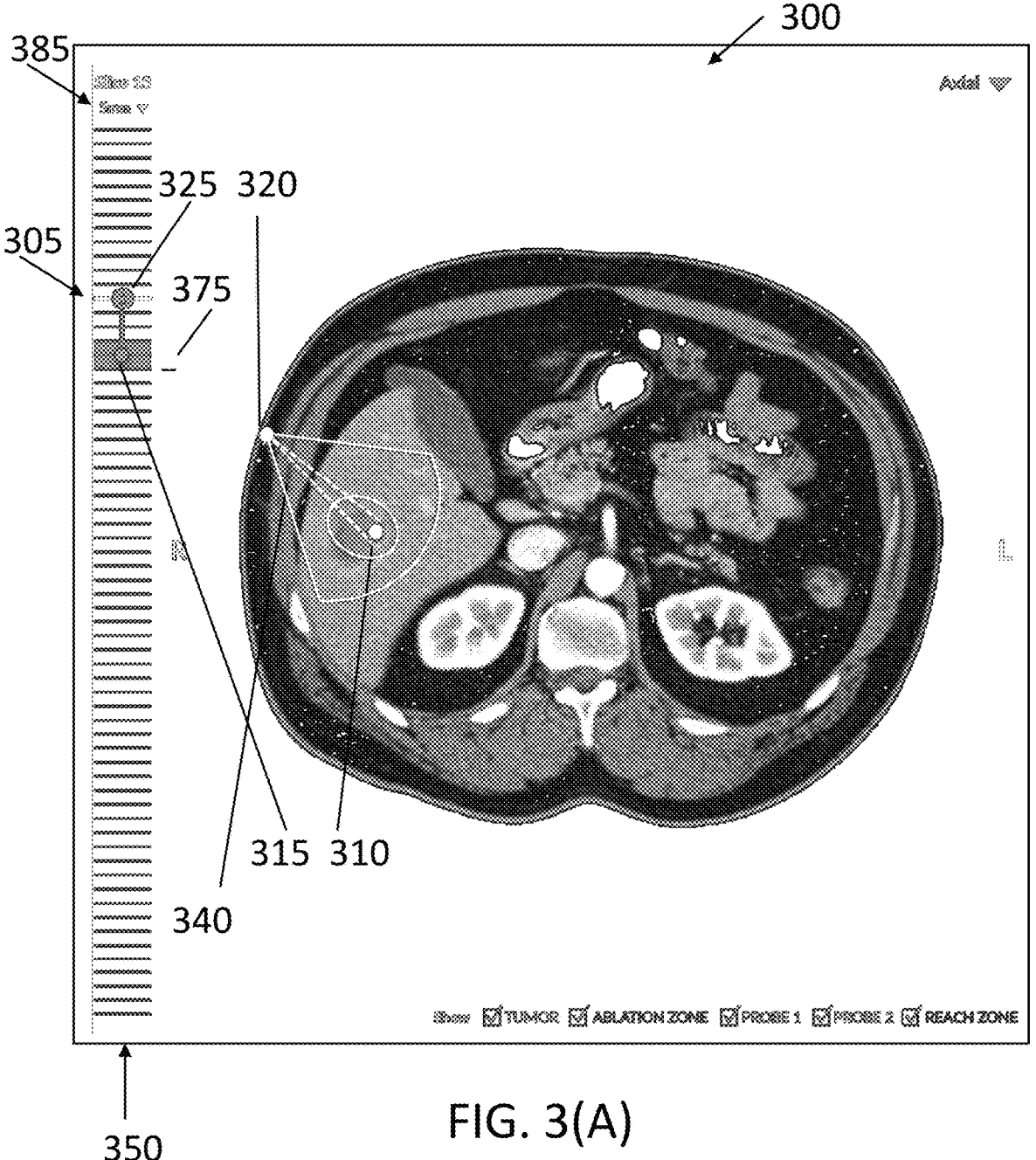
FIG. 3(A) is an illustration of a CT scan showing an axial 2D view and including an overlay providing 3D information and an indicator element.

Exemplary embodiments are described below with reference to the drawings. The present invention provides for improved visualization of image date where the image date is two-dimensional slices of three-dimensional (3D) image set. While many clinicians are comfortable paging through the various slices to obtain an understanding of the region of interest and surrounding tissue, as the planning and/or procedures become more complicated, the ability to visualize information from the 3D image set when viewing a two-dimensional (2D) image become important. Further, when there more than one 2D image mode, for example, showing from different perspectives or planes, the ability to visualize the data when looking at one image mode and then another (either 2D or the 3D data, and either sequentially viewing or having multiple image modes simultaneously on display) and/or have the ability to manipulate the data from within one image mode and see the changes within another image mode is also important.

For example, in some embodiments, a clinician will plan, perform, and/or evaluate performance FIG. 1 illustrates a system with displayed image data 100, a model system and cart 110, a device model 120, and registered device model 130 that can be overlaid on the displayed image data 100. In some embodiments, the planning image data 100 is a three-dimensional image set obtained from an imaging system (CT, MRI, etc.) 140. In some preferred embodiments, the three-dimensional image set is a medical image data set of an object that needs to be diagnosed and/or treated. The image software can allow for planning and assistance or automation in a diagnostic and/or treatment procedure by defining a needle trajectory by setting target and insertion point locations. Additionally, the imaging software may calculate an insertion depth based on the needle trajectory and the displayed image data 100. In some embodiments, the imaging software includes a device model 120. The device model 120 is a 3D model representation of the physical guidance device to be used in a procedure. The physical guidance device may be any suitable device for guiding a needle, probe or other medical device during preparation or performance of the procedure. The needle may be any suitable size or length needle for the procedure. In some embodiments, data corresponding to each needle of a plurality of needles or other medical device(s) is/are stored in the computing system as respective device models included in the imaging software.

The image data 100 comprises the 2D image presented to the clinician 200 as well as a 3D data set 210 extending along an axial direction 220, which generally corresponds, to the patient's bed (FIG. 2).

Figure 3B:
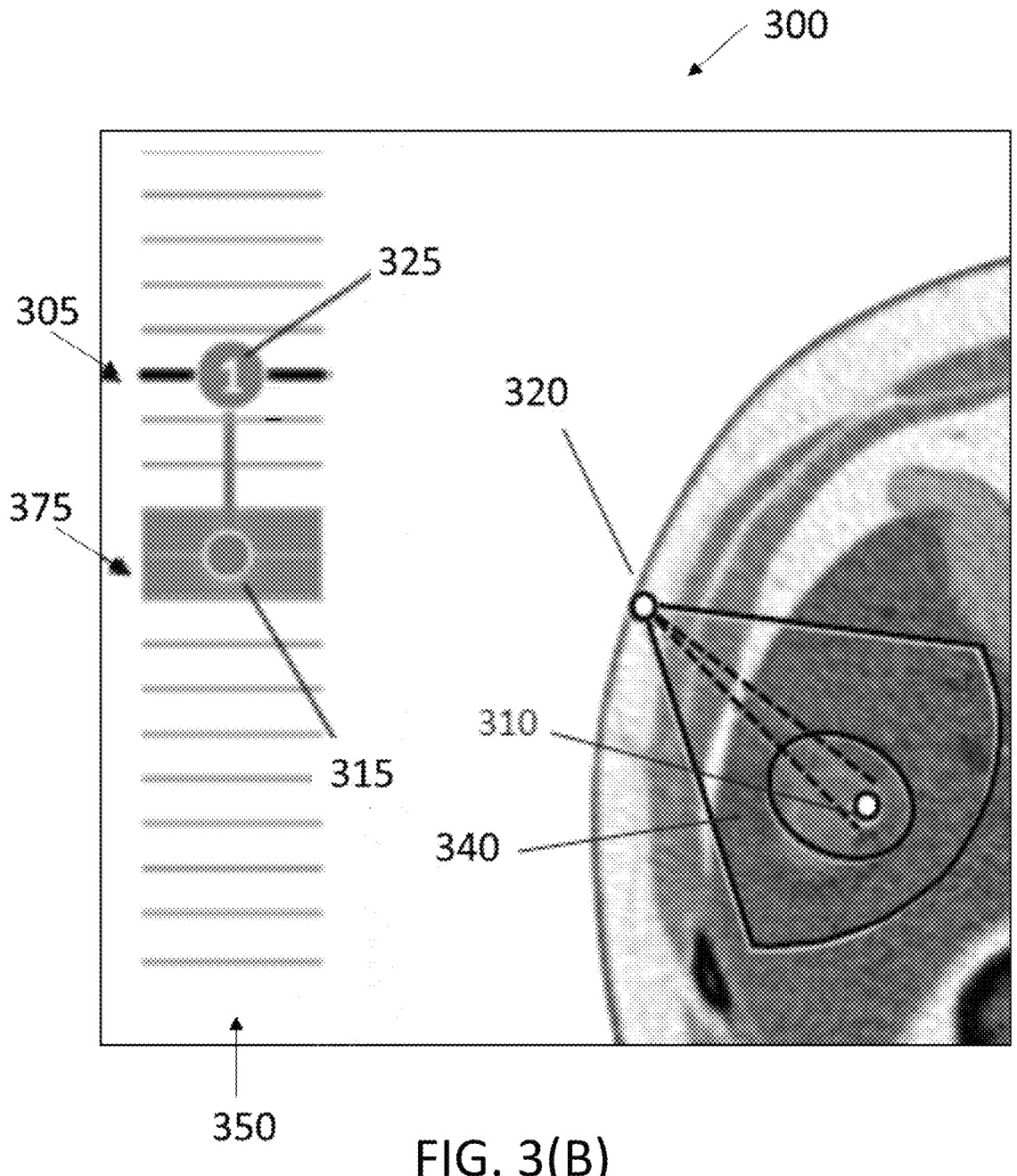
FIG. 3(B) is an expansion of the indicator element/indicator bar and region of interest from FIG. 3(A).

FIG. 3(A) and, with the region of interest enlarged for better viewing, FIG. 3(B) provides a visualized image slice 300 which is a 2D CT image of a patient. The image mode shown in this figure is of is of an axial view. Both a target point 310 and an insertion point 320 are identified in this image. A probe trajectory 340 is defined by the line between the target point 310 and the insertion point 320. The broken line provides the probe trajectory 340 in other 2D slices.

On the side of the visualized image slice 300, an indicator element 350 is provided where the location of the slice image in the 3D image data set is indicated. This indicator element is shown as an indicator bar. In addition to showing the location of the visualized slice 305 with a thicker line (and/or with a different color line, a marker, a blinking line, etc.), the depth and expansion of the region of interest 375 through multiple slices is shown in the indicator bar as well. A target point marker 315 and an insertion point marker 325. This facilitates easy viewing, planning, and procedure, particularly for describing depth information, since the 2D image does not facilitate an easy understanding of the depth of various features within the image when the doctor or technician is viewing the 3D image set by viewing the 2D image slices sequentially. For the CT image slice of FIG. 3(A), the thickness of the slice is indicated by the spacing of the lines on the indicator element 350, where the number of slices within the 3-dimensional image set is indicated by the number of horizontal lines in the indicator element.

For an axial image, the lines making up the indicator bar can indicate each slice in the 3D scan (for larger data sets, a single line could be indicative of 2, 3, 4, 5, etc. slices). For other image types, the lines are not CT image slices taken from the three-dimensional image set since the data is shown in a different plane. These may be the sagittal or coronal planes or having the same coordinate system as the axial image mode, or may be virtual slices within the plane of the image mode shown. These rendered slices are out-of-plane compared to the three-dimensional image set and provide information that the clinician needs to make decisions based on the image data in a way that can be much more informative or more intuitive than the views that are only in-plane.

Thus, imaging apparatus and software allows for, for example, the planning, performance, and evaluation of the insertion of one or more biopsy or ablation probes. The software can load images scanned by an imaging system 140 (e.g., a CT scanner) and shows them on a display 100. The clinician, such as a doctor or technician can set planning information (e.g. insertion point, target point).

To display the slice image 300, the imaging software draws one of the axial slices scanned by the imaging system 140 on a display. The imaging software also draws an indicator element 350, which provides information as to which axial slice is displayed. In this embodiment, the indicator element 350 is a side bar that is overlaid on the left side of the slice. However, in other embodiments, the indicator element 350 may be located, for example, above, below, or to the right of the slice image. Additionally, in some embodiments, the location of the indicator element 350 may be moved by the user via the input device (e.g., by clicking or dragging the indicator element.) In other embodiments, the content of the indicator element 350 may be zoomed in or out to see more or less of the full bar length (i.e., more or less of the scope of the three-dimensional image set).

The image 300 being displayed may be controlled by the user with an input device. The indicator element 350 provide the location of the slice 305 within the 3D image data provided by the imaging system 140 by marking the location of the slice 305 within the full three-dimensional image set shown by the indicator element 350. This feature enables users to know which image slice 300 is shown in the display. Software may also show slice information 380 (e.g. thickness, the number of slices) as shown in FIG. 3(A) in the upper left. The input device may be, for example, a mouse, a touch screen, a keyboard, keypad, microphone, monitor, speaker, still camera, stylus, tablet, touch screen, trackball, video camera or other movement sensor, etc.

In use, as the user scrolls or otherwise moves through various slice images 300, the location of the visualized slice 305 moved along the indicator element 350 to show where the slice is relative to the other slice images. As the user scrolls along the indicator element 350 using the input device, the slice image being visualized 300 will change to correspond to the slice image of the slice indicated on the indicator element 350 as marked with the thick line or other indication visualized slice 305. Similarly, if additional two-dimensional images are displayed, the images being displayed may change to correspond to the slice image of the slice indicated on the indicator element 350.

The imaging software, such as the imaging software described in U.S. Pat. No. 10,695,132 herein incorporated by reference, enables the user to designate a target position, such as a tumor. After the user, for example, click on a tumor in each relevant slice, the imaging software overlays designated zone on the slice image being displayed 300 and updates the indicator element 350 to show depth of tumor. This information can be used by the user to plan and define one or more trajectory for biopsy or treatment.

Where more than one needle will be used in the treatment or biopsy, there may be an indication of more than one target points or more than one insertion points to account for each of the needles used in, for example, the ablation therapy. The user can set insertion point and target point of a trajectory by, for example, clicking with a pointer element on the slice image or by touching the display screen having touch capabilities. The software overlays the insertion point(s), target point(s) and optionally a path between the two on any slices. Path may be curved when a curved probe is used.

The imaging software, in addition to or as an alternative to defining the target point 310 and an insertion point 320 for planning the insertion or insertions, may also define the full region of interest 370 within the image. This can be done by requesting that the user input the information in any of the 2D images within the 3D image data to define the tumor region or region of interest.

In some embodiments, all the information defining the target point, insertion points, and optionally region of interest is specifically defined by the user. In other embodiments, some of this information can be obtained through an algorithm. For example, the user can indicate the tumor on one slice and the algorithm defines the dimensions of the region of interest based on the tumor boundary. Alternatively, the region of interest can be described as the tumor combined with a margin around the tumor that has a set or adjustable size (e.g., 1 mm, 2 mm, 3 mm or more). In another example, the user defines a single target point and the format for multiple probes (e.g., the format for three probes is a triangular pattern, centered around the selected target point). In this example, the display may be either the single target point or the three distinct points defined by the triangle and the distance between the probes (see U.S. Pat. No. 10,695, 132).

When the procedure is an ablation, the user may select probe type, size, length, power, duration and the number of probes. Then, software can overlay expected ablation zone on the slice image as well. Users are able to compare expected ablation zone and designated tumor on each slice.

This invention can be used in conjunction with a guidance device that is used to guide one or more needles in a percutaneous procedure. The device includes fiducial markers, which may be visible in the display. Because they are placed uniquely in 3D coordinates, software is able to register the device in, e.g., CT images. This software updates the indicator element to show slices where fiducial markers exist. Software may overlay reachable area when users use the device.

In some embodiments, the indicator element 350 may have more or less information and indicated in a variety of manners. For example, the location of the slice image in the 3D image data set 305 is indicated by an arrow in FIG. 4(A) and a thicker line in FIG. 4(B). The depth, or number of slices where a region of interest is found within the various image slices is also shown by the region of interest marker 375, along with target point marker 315 and the insertion point marker 325.

Figures 4A, 4B, 4C:
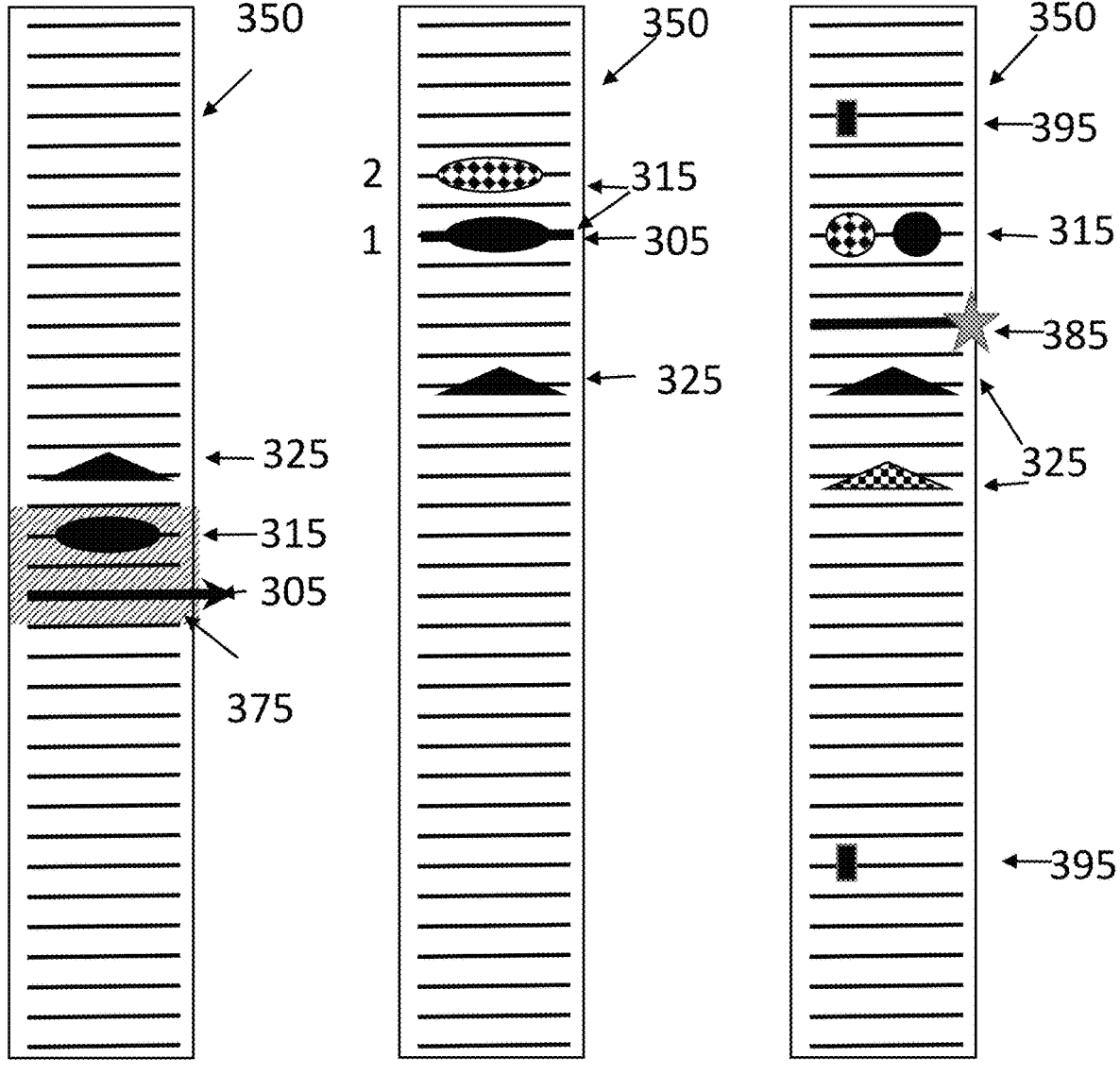
FIGS. 4(A), 4(B) and 4(C) are illustrations of different embodiments of the indicator element

In the embodiment exemplified by FIG. 4(B), the indicator element 350 has two separate target point markers 315. These are indicated by different patterned oval but could be distinguished by color, numerical labels, etc. Similarly, FIG. 4(C) depicts two separate target point markers 315 that, in this embodiment, occur on the same slice. The two separate target point markers 315 correlate with two separate insertion points 320 in the image 300 (not shown). This embodiment also provides an indication of a "favorite" or interesting slice 385 that may be defined by the user.

Similar to the various means of identification or marking of the current slice 305, target point markers 315, insertion point markers 325, region of interest markers 375, favorite slice markers 385, other markers such as markers for the location(s) of the fiducial marker 395 means may be equally applicable. Other configurations such as color can be used as marker types to distinguish and provide information about the various features on the indicator element 350.

Information provided in the slice image 300 may include the insertion point, the region of interest, the region of interest, an ablation zone, a reachable zone (e.g., the volume of tissue reachable by a specified needle via the system from the defined insertion point). Probe (e.g., needle) trajectories as planned or as executed may be indicated as well. Fiducial markers, either detected automatically or manually may also be provided.

In some embodiments, information pertaining to slices not being displayed may also be provided in the slice image 300. For example, a probe trajectory may continue through multiple slices (three in FIG. 4(A) and eight in FIG. 4(B). This may be indicated, for example, a solid line for the probe trajectory in the displayed slice and a transparent, grey, or dashed line for the probe trajectory as it travels through a non-displayed slice. Additionally, if a curved probe is to be used, a curved trajectory may be indicated by a similar means.

In yet other embodiments, the location of the fiducial markers 395 within the three-dimensional image set may be displayed in the indicator element 350. Other information that may be included in the indicator element includes grids, gridlines, etc.

In addition to the axial image shown in, for example, FIG. 3(A), other image modes may also be displayed with or instead of the previously described axial view. For example, one or more of the axial, sagittal and coronal image modes may be shown. These modes are known as MPR (Multi Planar Reconstruction). Axial, Sagittal and/or Coronal views are linked each other as shown in the three plans of FIG. 5(A). Each view can have indicators (which may be sidebars as shown in FIG. 4(A)-(C) or one or more may be a different indicator element) and guidance application visualizes relative position on them. For example, the indicator element on the axial image mode can show the position of Sagittal and/or Coronal views.

Another image mode is the Arc image mode, or Arc view. This image mode is illustrated in FIG. 5(B) and is a rotational view synchronized with a plane of an arc in a guidance device 502, such as the needle guidance device described in patents and applications described herein above. The guidance device 502 having an arc portion 504 that can be positioned onto the patient and is preferably connected to a guidance application that is configured to read the angle of the arc portion of the device 504 as it rotates around the center of the guidance device 502, creating axis 506, and update images on the display. Therefore, rotational angle of the device can be synchronized to the image on the display.

This image mode enables the user to easily find a plane to insert a probe/needle where the user may easily look for the center of tumor and adjust the trajectory. The Arc image mode is an out-of-plane image mode that is particularly useful for visualizing the insertion plane and can be compared with the physical rotation seen on the guidance device. The indicator elements allow the user to readily understand how the plane of the arc of the guidance device relates to the three dimensional data. In embodiments where the registration of the guidance device to the patient is not completed, guidance device position may be estimated based on the known information that the insertion point is at the center of the device (axis 506).

The Trajectory image mode (trajectory view) is similar to Arc View and its orientation is illustrated in FIG. 5(C). Trajectory view is a rotational view with a trajectory of the needle as a rotational axis and is shown as vector 508. The user is able to rotate trajectory view and confirm critical sections (e.g. vessel) and/or interests (e.g. tumor) around the trajectory in this view. In use, the user may adjust the trajectory by this view. For example, the ablation time and/or power while planning and/or performing an ablation therapy could be adjusted if vessel is near the trajectory 508 due to the vessel transferring heat. The Trajectory image mode is an out-of-plane image mode that can provide great advantage to the clinician when used with (or instead of) the in-plane modes. However, since clinicians and other users are not used to viewing the three-dimensional image set using this imaging mode, the addition of the indicator elements provide additional information of how the displayed image data in the Trajectory image mode relates and is situated within the patient. This allows for both improved understanding about the location of the displayed image data within the patient and improved ability to manipulate the data to view different images and obtain an overall understanding of the planned procedure.

The Base image mode (base view) is based on the guidance device as illustrated in FIG. 5(D). The guidance device 502 used to construct the Base image mode has fiducial markers, which, for example, are visible in CT images. Thus, in embodiments using CT, a guidance application registers the guidance device in a CT volume and find the device direction within the volume. The Base image mode shows a parallel plane respect to base of the device, as shown in FIG. 5(D). This imaging mode can be used to visualize detected fiducial markers and enables the user to confirm registration result in this process. Because Base image mode and Axial (or Sagittal/Coronal) image modes are independent, the Base image mode can also include one more lines corresponding to the axial (and/or sagittal/coronal) planes. Pitch of lines may be adjustable, or fixed length. Lines might be tilted.

Flythrough image mode is in a perpendicular plane respect to a trajectory, as shown in FIG. 5(E). This image mode, for example, enables the user to confirm critical sections around a trajectory 508 since it can show every plan perpendicular to and centered around the trajectory 508 as it moves long the axis 510. The Flythrough image mode is an out-of-plane image mode that can provide great advantage to the clinician when used with (or instead of) the in-plane modes. As with the Trajectory mode, while using this out-of-plane imaging mode, it may be difficult for the clinicians and other users to obtain a good sense of location and movement through the three-dimensional image set, so the indicator elements provide useful information of how the displayed image data in the Flythrough image mode relates and is situated within the patient. This allows for both improved understanding about the location of the displayed image data within the patient and improved ability to manipulate the data to view different images and obtain an overall understanding of the planned procedure. Flythrough image mode can have a particular benefit when a trajectory is, at least in part, directed through hollow shaped structure. Of note, Flythrough image mode is not able to visualize whole trajectory on single image. Thus, adding an indicator element to show the depth of the portion of the trajectory shown in the flythrough image mode can be particularly useful to a user.

Figures 6A, 6B, 6C, 6D, 6E, 6F, 6G, 6H, 6I, 6J:
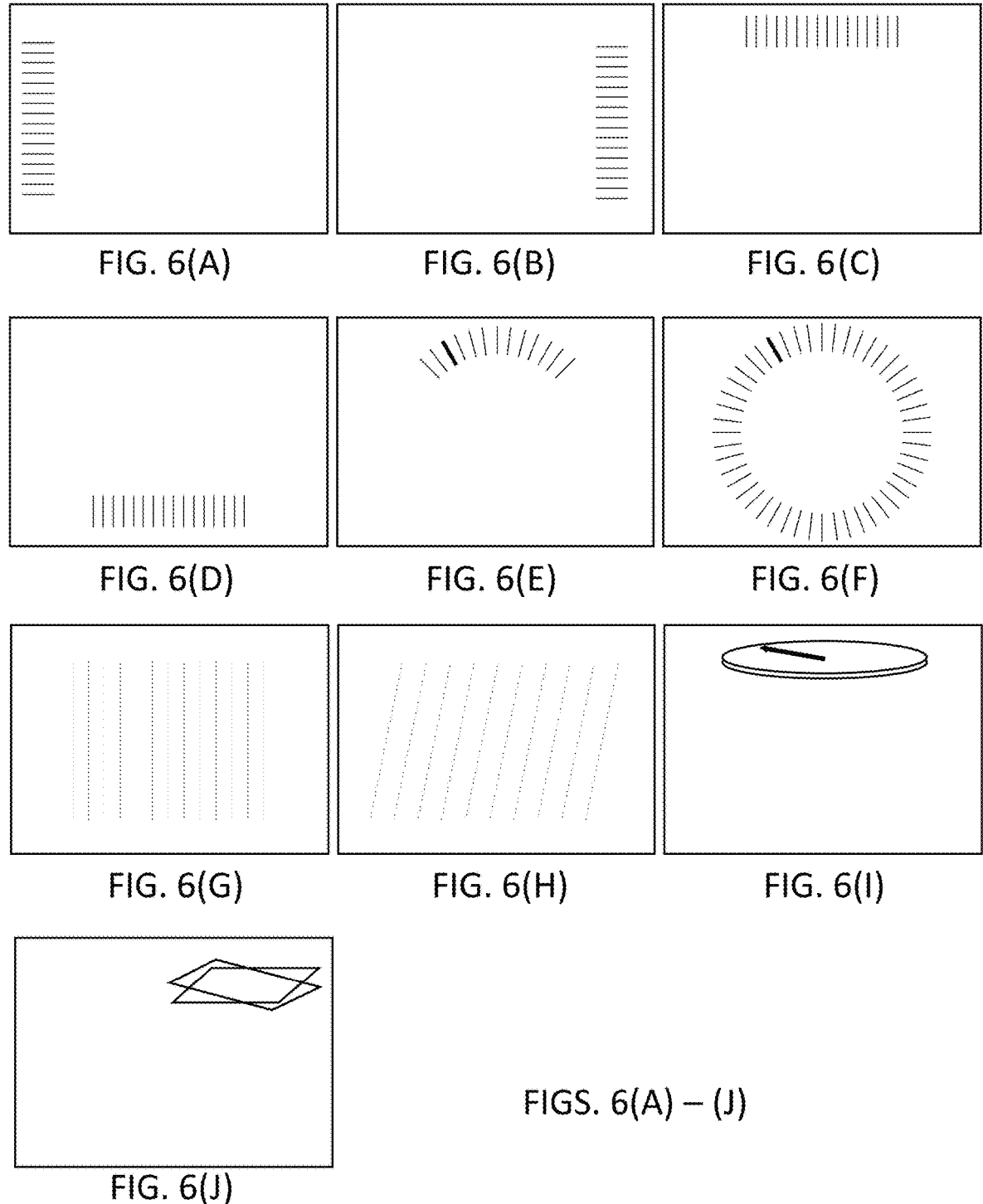
FIGS. 6(A)-6(J) provide multiple variations for indicator elements that may be used for the various visualization modes as described herein.

FIG. 6(A)-6(J) show several variations for different indicators. FIGS. 6(A), (B), (C) and (D) are sidebars indicators, where they can be located at different locations on the image. FIG. 6(A)-(D) are applicable, for example, for navigating parallel slice views. FIG. 6(E) is a curved indicator bar. FIG. 6(F) is a closed bar. FIG. 6(E)-(F) are applicable, for example, for navigating views that rotate around a common axis. This type of indicator can be located in the corner of the view area, surrounding the image within the view area—either outside the image or as a full or partial overlay. FIGS. 6(G) and (H) are overlay lines, where the indicator element may be shown as an overlay of part or all of the visualized slice. FIGS. 6(G) and (H) are applicable for navigating other image views relative to the current image view plane. In some embodiments, and particularly for the overlay indicators, the opacity for each indicator can be adjusted. This enables to see images under the indicator. FIG. 6(I) is a 3D image that can be used to visualize angle. This is a 3D visualization of the plane view of the indicator shown in FIG. 6(F). FIG. 6(J) is an icon to visualize relative angle.

Figure 7A:
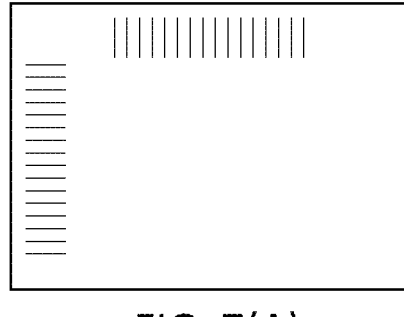
FIGS. 7(A)-7(C) provide multiple variations for multiple indicator elements in a viewing mode and for multiple viewing modes with indicator elements as described herein.
Figure 7B:
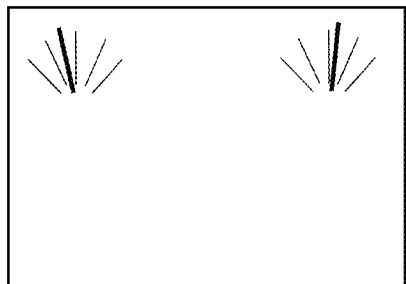
Figure 7C:
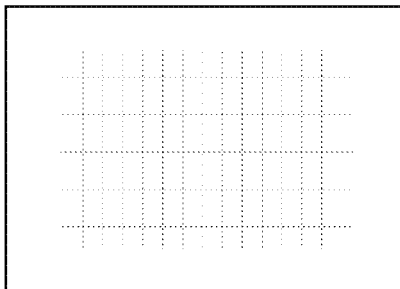

FIG. 7 shows examples of combination where more than one indicator element may be used in a single image mode. FIG. 7(A) has two bars in single view. FIG. 7(B) has two curved bars in single view. FIG. 7(C) has two overlay lines as grid. Combining multiple indicators in a single view provides, for example, a reference to the other views within the same screen and can give relative orientations based on different rotation axes. These can be used simply for understand the relative orientations or for changing the visualized image slice based on information in indicator element.

Figures 8, 9A, 9B:
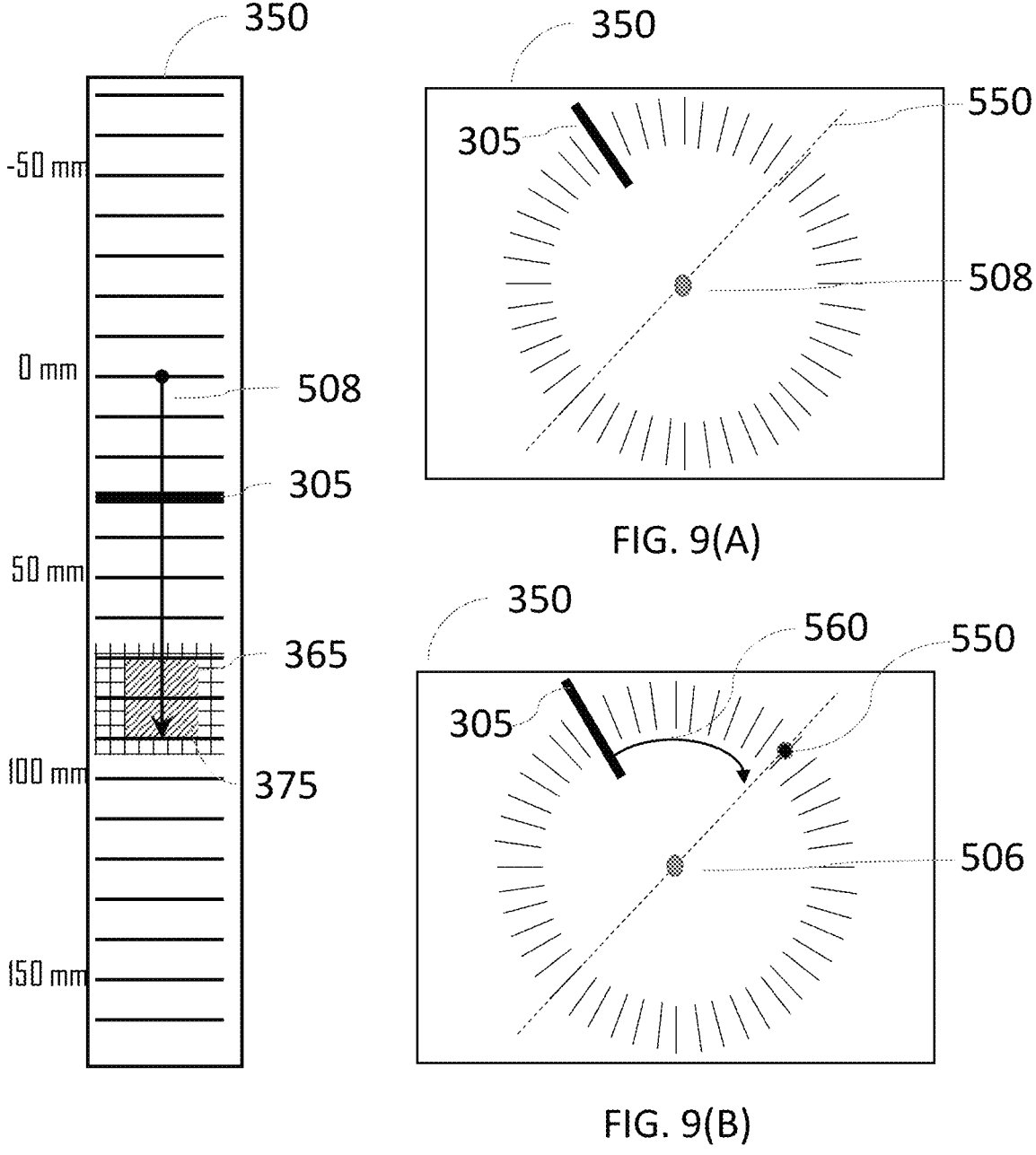
FIG. 8 is an illustration of an embodiments of the indicator element that is a vertical bar in Flythrough image mode.
FIGS. 9(A) and 9(B) are illustrations of embodiments of the indicator element for various image modes.

FIG. 8 is an exemplary vertical bar indicator for a flythrough image mode. This bar visualizes a trajectory and depth of the trajectory on the visualized slice. In this embodiment, the indicator bar 350 has scale shown on the left and its unit is millimeter, where the '0 mm' position is set at the insertion point of a selected trajectory. The trajectory 508 is visualized as an arrow, insertion point is at '0 mm' position and tip of the probe is at '+90 mm' position. The thick line 305 indicates that the location of the visualized slice in a corresponding image is at '+30 mm' position in this figure. A region of interest marker 375 is shown, to indicate the interest in a segmented tumor and ablation estimated zone 365 exist around the tip.

FIG. 9(A) is an exemplary closed bar indicator 350 for a Trajectory image mode. The closed bar indicator 350 can always show the current view slice 305 that can be changed as the view rotates around the trajectory axis 508.

FIG. 9(B) is an exemplary closed bar indicator 350 for the Arc image mode. The closed bar indicator can always show the current view slice 305, the target Arc slice 550 which is the slice in which the arc portion of the guidance device is located. The arc rotation direction 560 of the guidance device is also shown. The curved arrow 560 denotes rotation around the arc axis 506.

Guidance application, when used in combination with the image modes and indicator elements as disclosed herein, provides customizable interface. Users are able to use single view and/or combination of views. All views are preferably linked each other.

Figure 10A:
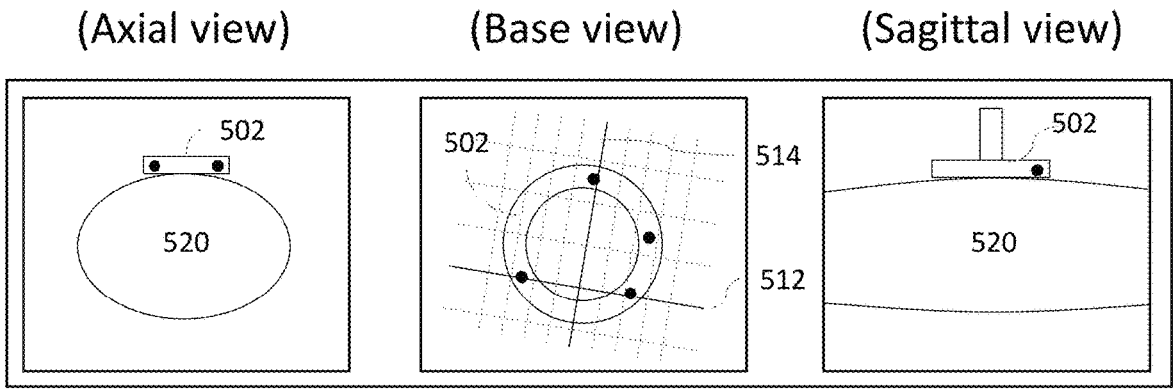
FIGS. 10(A) and 10(B) show linked Axial, Base and Sagittal image modes, where the Base image mode includes a grid with a grid showing the plane and location of the linked Axial and Sagittal image modes.
Figure 10:
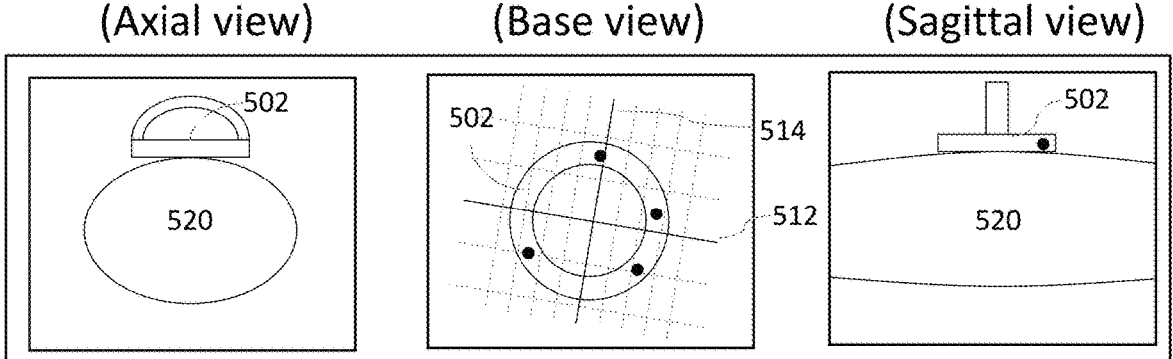

FIG. 10(A) shows linked Axial, Base, and Sagittal views, where the Axial view shows the guidance device 502 located on the patient 520. The Base view has a grid for which the horizontal lines on the Base image mode correspond to axial plane where the line 512 is linked to the showing axial slice. Vertical lines correspond to Sagittal plane, where the thick line 514 in the Base image mode is linked to the sagittal slice in the sagittal image view. This image mode also has image or icon denoting the guidance device 502 with one or more fiducials markers indicated as dark dots. The Sagittal view of FIG. 10(A) also shows the patient 520 with the location of the guidance device. FIG. 10(B) is of the same data set, but the location of the location of the visualized axial slice shown in the Axial image mode is different. This is made obvious by the portion of guidance device 502 shown in each image. In some embodiments, the guidance application is configured to update the grid of the Base image mode in real time, or with a slight delay, when the user controls the displayed image within the axial image mode.

The indicator elements can be used to facilitate linking between the different image modes and user-directed changes to the multiple images being visualized. For example, if users set to visualize Sagittal plane on Axial image mode, controls on sagittal view propagate to the indicator on axial image mode and the visualized image shown on the axial image mode will move to the image corresponding to the location of the 2D image intersecting with the visualized image within the Sagittal image mode. In another example, as the user propagates down the selected out-of-plane trajectory while visualizing the Flythrough image mode, the image displayed in an axial image mode will change in real time (or close to real time) to correspond to the axial image that intersects with the flythrough image being visualized.

Figure 11A:
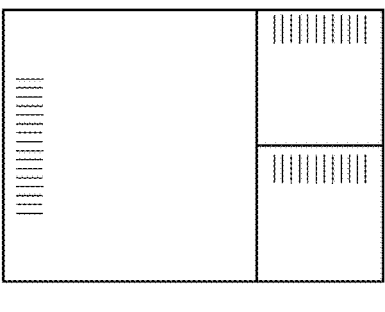
FIGS. 11(A)-11(B).
Figure 11B:
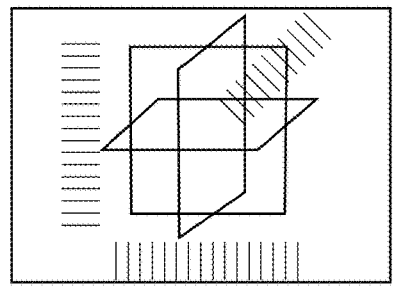

FIG. 11(A) illustrates an embodiment that contains three image modes, each with an indictor bar. Each image mode has a separate location on a display/screen. Thus, a first, second, and third image slice in a first, second, and third mode can be displayed simultaneously on the display/screen and each has their own indicator element that helps describe the relationship between the different image slices as shown it the various image modes. FIG. 11(B) shows a different way of visualizing the image using a three dimensional view with three different indicator elements for each of the three cardinal directions. Three views are combined in 3D space in a single view along with three separate indicator elements—one for each of axial, sagittal, and coronal image modes (or axial, base, and flythrough; or base, flythrough and trajectory, etc.). Thus, as discussed above, the user may manipulate the image by using the indicator element within one image mode to alter the other image modes being displayed, and in addition, the user may move (or alternate) between the different image modes to manipulate the visualized images in all of the different views by adjusting the position from only a single indicator element.

This invention enables to visualize depth, length, position, relative position, movement, angle, relative angle and so on. If similar indicators show different things, it could make users confusing.

Different things should be visualized by different indicator elements. For example, depth is visualized by vertical bar, relative position is visualized by horizontal bar, and angle is visualized by curved bar. In another case, two relative positions are visualized by vertical and horizontal bars. Any one or combination of indicator elements may be used depending on the need for movement within an image mode or between various displayed image modes.

Figures 12A, 12B:
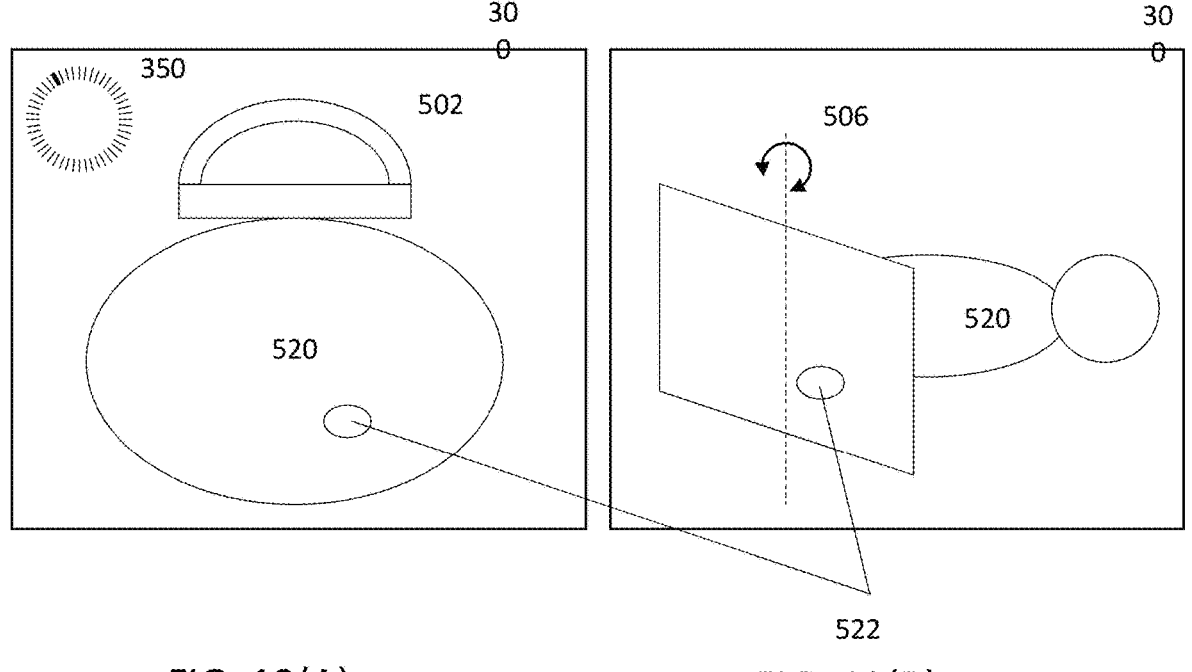
FIG. 12 shows an Arc image mode (FIG. 12(A)) and a linked 3D view in FIG. 12(B).

FIG. 12 shows the Arc image mode (FIG. 12(A)) and linked 3D image mode (FIG. 12(B)). FIG. 12(A) includes the Arc image mode and an Arc indicator which visualizes angle of the arc on the guidance device. The indicator element 350 is illustrated on left top corner as a circle shaped indicator having one thick line showing the angle of the visualized slice 300. Users are able to change angle and thus the visualized slice 300 by rotating the connected guidance device which is shown in the visualized slice 300 as 502 located on the patient 520. A guidance application can then read the angle of the guidance device periodically and update the Arc view to show the visualized image slice associated with the angle of the guidance device. The 3D view, in this embodiment, is shown in FIG. 12(B) and visualizes a segmented tumor 522, the patient image generated from scanned images, and Arc view on the corresponding plane. Guidance application also updates 3D view. Arc view rotates around the axis 506 in 3D space. And, 3D view may overlay 3D image of the device.

In some embodiments, the device is rotated virtually through an indicator element showing the device 502 or through user interface of the application. If a Trajectory view mode is shown, it can be linked similarly. The difference between the Arc view and Trajectory view is a rotational axis, where the axis for the trajectory view is the planned or actual trajectory for an ablation, biopsy, or other procedure and the axis for the Arc view is the axis defined by the guidance device.

Figure 13A:
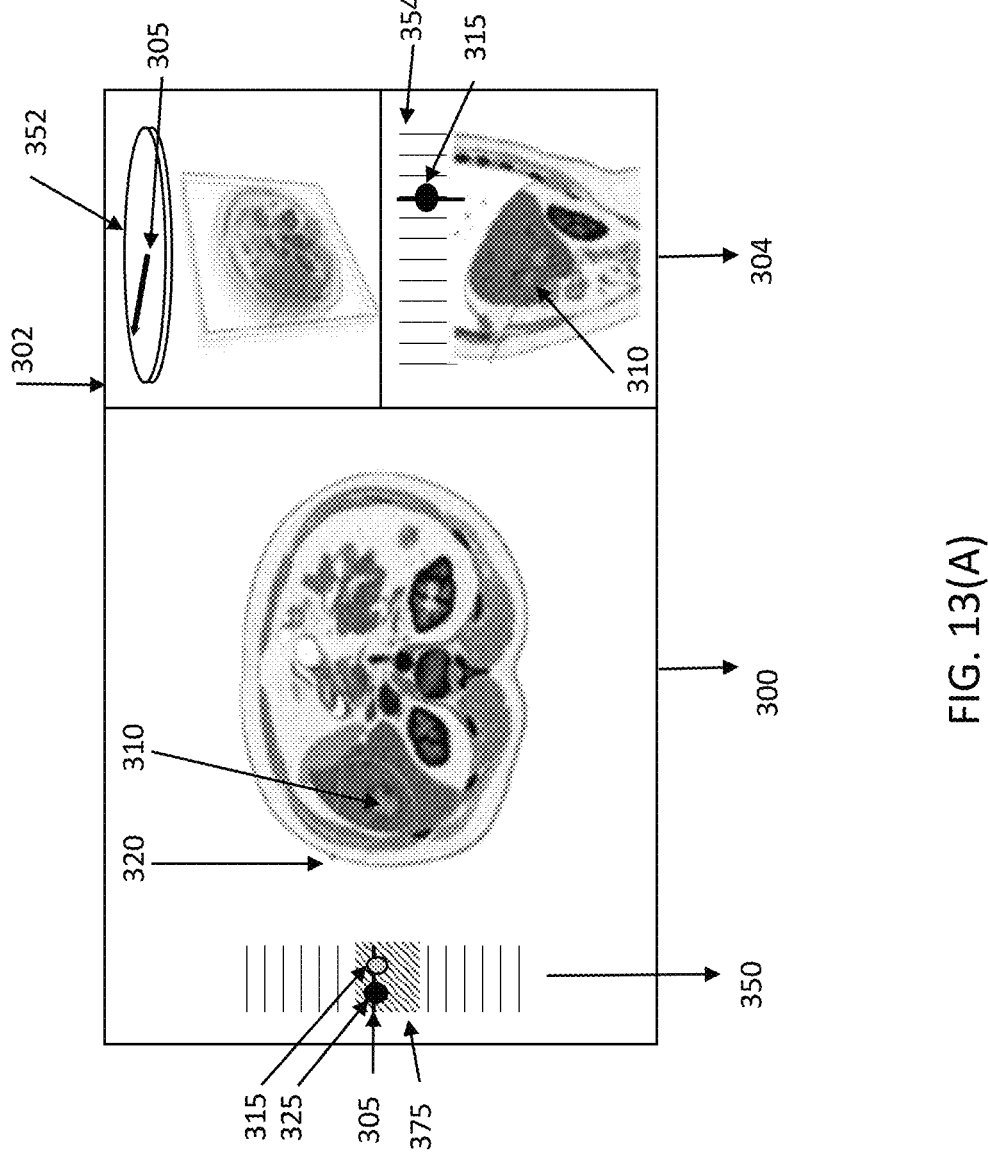
FIG. 13(A) is an exemplary screen shot of a planning software providing a CT scan including overlays for each image mode providing relative 3D information.

FIG. 13(A) is a screen shot of the output of an imaging software system showing a 2D image slice 300 in an axial image mode and an indicator element 350. Additional image modes of the slice image are shown 302 (3D Preview mode) and 304 insertion plane mode as well as additional information for planning and surgery. In this case, the target point 310 is shown as a tumor in the object to be treated (i.e., the liver) with a proposed insertion point 320 for needle entry for an ablation therapy. The visualized image slice 300 is a slice where both the target point 310 and the insertion point 320 are both visible. Thus, the indicator element 350, at the location of the visualized slice 305, also contains both the target point marker 315 and the insertion point marker 325. Visualized image slice 304 also contains the target point 310, so the indicator element 354 has the visualized slice 305 and target point marker 315 at the same position.

In some embodiments, the user scans through the various slice images by, for example, clicking with a pointing device on the location of the indicator element 350 indicating the slice to be viewed (the visualized image slice). In this instance, when a different slice is selected, both the image slice 300 displayed as well as the additional views of the image data 302 and 304 are displayed are the slice indicated by the location on the indicator element. Alternatively, the user may scroll through the images of the two-dimensional image slices 300 from within the main viewing window or an additional view of the image data set 302.

The horizontal lines on the indicator element 350 shown in FIG. 13(A) indicate each image slice within the three-dimensional image set. The slice width of the two-dimensional images within the three-dimensional image set is indicated by the spacing of the horizontal lines within the indicator element. If the image set is created having, for example, 2 mm slices instead of 5 mm slices, the number of horizontal lines indicating the number of two-dimensional image slices may be greater. The indicators elements 352 and 354 for the additional views of the image data set 302 and 304 in FIG. 13(A) provide information about the image slice view within the image set for other view orientations. Of note, the image slice may or may not refer to an actual slice, such as created by a CT or they may refer to a slice created by rendering the 3D image into the image mode of interest.

Figure 13B:
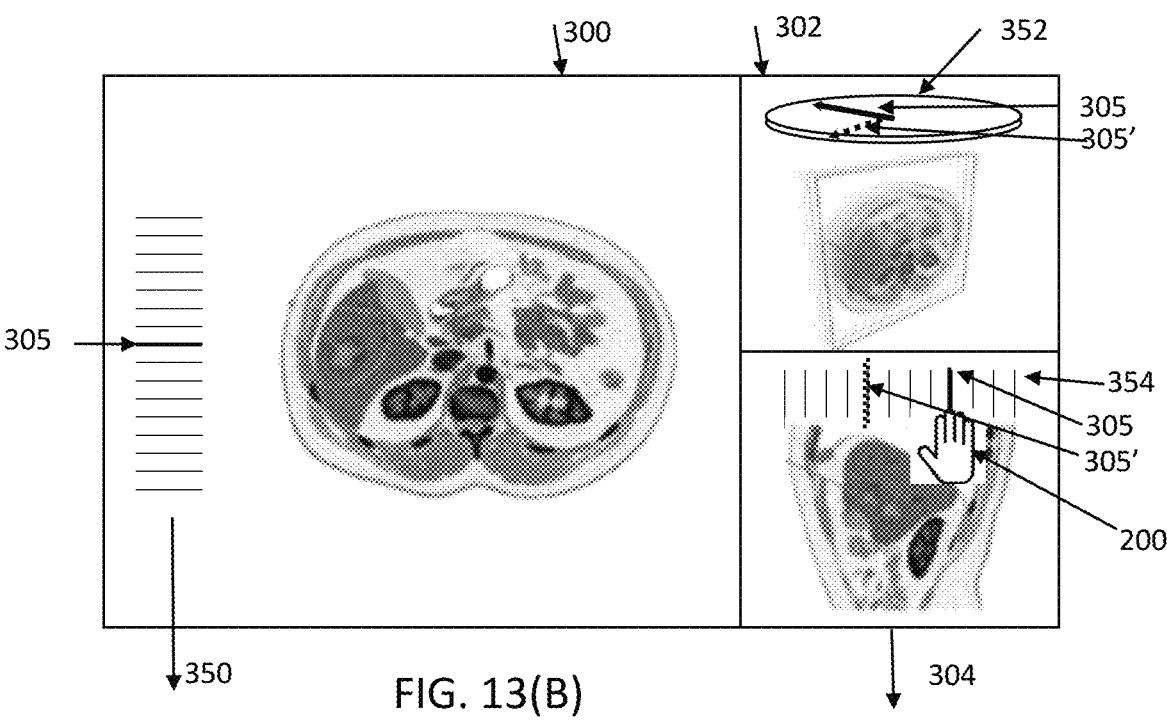
FIG. 13(B) is the exemplary screen shot shown in FIG. 13(A) showing additional relationships.

With FIG. 13(B), one can see the interactivity between the different visualized image slices 300, 302, and 304. If the clinician 200 proceeds to select the visualized slice 305 within the visualized image 304 and drag it to the left, not only will the visualized image 304 update through the slice stack to the indicated slice 305', but the visualized images 300 and 302 are similarly updated—if the new view to which the clinician moved relates to new positions in these images, through their real or rendered slice stack, changing both the displayed visualize images 302 and 304, the indicated slice 305 to new indicated slice 305'. In this example, visualized slice 300 is not changed in the update. Additionally, the presence or absence of the various markers (not shown) may be updated in the indicator element as applicable to the current display.

Figure 13C:
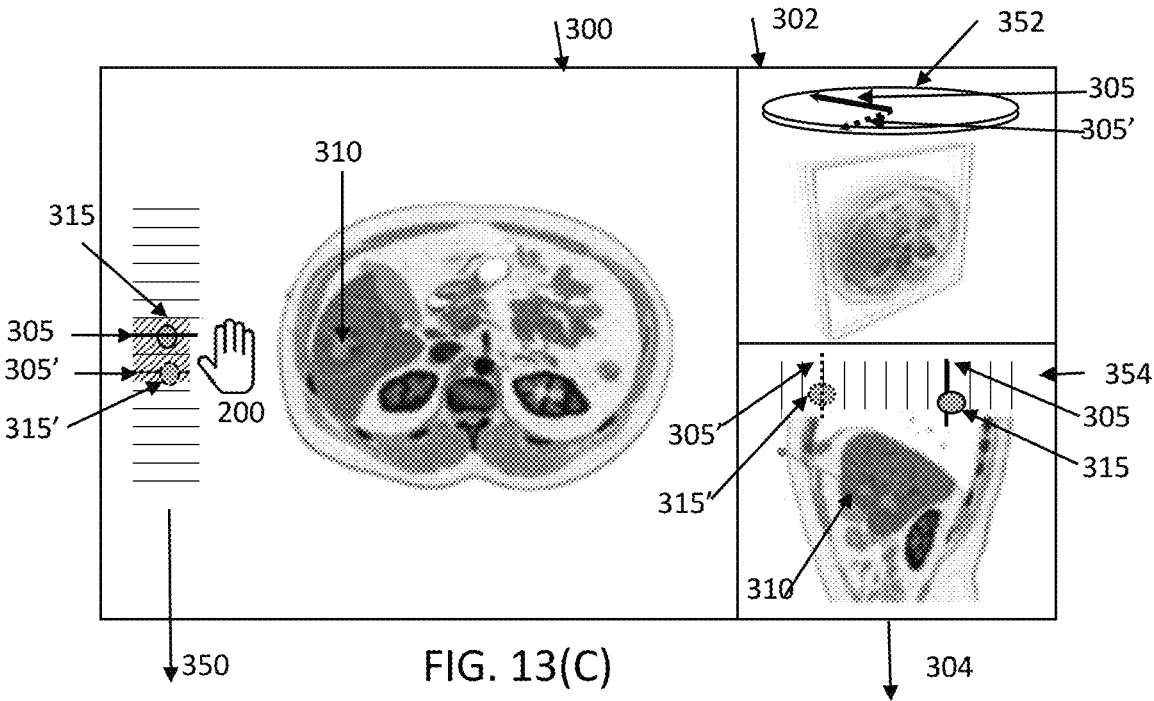
FIG. 13(C) is the exemplary screen shot shown in FIG. 13(A) showing additional relationships.

In FIG. 13(C), another embodiment with interactivity between the different visualized image slices 300, 302, and 304, is illustrated where the clinician 200 proceeds to select the target point marker 315 within the visualized image 300 and, in order to change a change in the planned target point 310, drag the target point marker 315 down to the new location 315'. With this movement, the visualized image 300 will update through the slice stack to the indicated slice 305'. Also, visualized images 302 and 304 are similarly updated, through their real or rendered slice stack, changing both the displayed visualize images 302 and 304, and the indicated slice 305'. The updated target point marker 315' is now seen in the indicator element 354 showing where the updated point would be located in the updated display. Similarly, in visualized image 302, the indicator slice 305 is updated to indicator slice 305'.

Other exemplary ways the user can interact with the various markers on the indicator elements 350, 352, 354 are provided in Table 1. As noted, the ways the interaction may occur are dependent on the mode of the visualized image slice.

TABLE 1

| Marker Interaction | Effect on Image View |
|---|---|
| Current view slice | |
| Select | Jump to selected slice |
| Drag | Scroll through slice stack |

TABLE 1-continued

| Marker Interaction | Effect on Image View |
|---|---|
| Target/Insertion point | |
| Select | Jump to slice(s) at point |
| Drag | Move point normal to slice |
| | Trajectory line |
| Select | Switch to trajectory view |
| | Region of interest |
| Select | Jump to center slice |
| Drag border | Change region size |
| | Region of interest margin |
| Drag border | Change margin size |
| | Ablation zone |
| Drag border | Change ablation zone size |
| | All |
| Hover | Highlight corresponding overlay |

Figure 14:
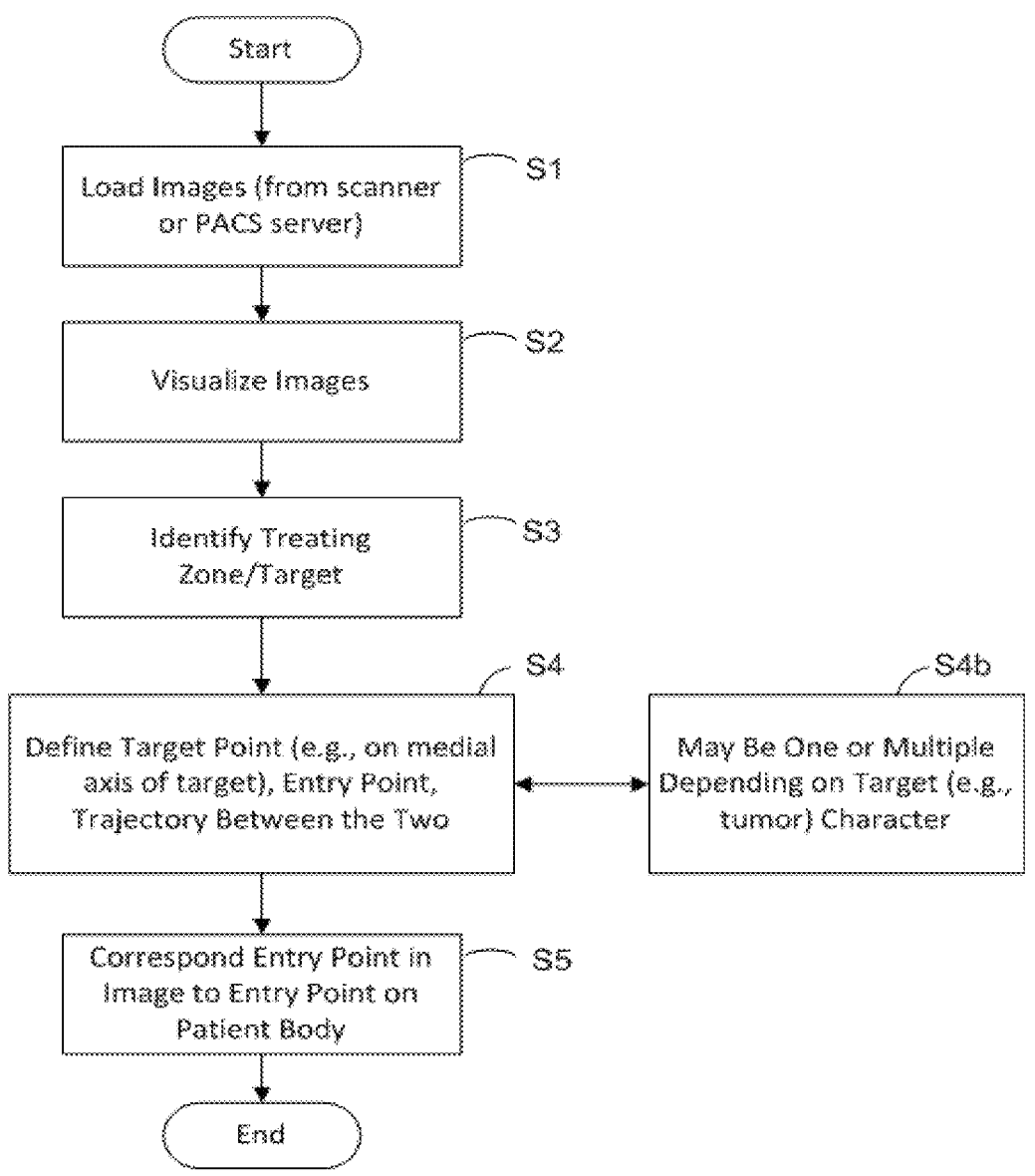
FIG. 14 is a flow chart showing at least one embodiment of a method for performing ablation and/or needle guidance planning and/or performance in accordance with one or more aspects of the present disclosure.

In an exemplary ablation procedure described in FIG. 14, the clinician may use the imaging software system for processes including ablation planning and performance steps, including, but not limited to, one or more of the following: (i) loading images (e.g., from a scanner, a PACS or other scanning device/system, or using a fresh or newly scanned image) (see step S1 in FIG. 14); (ii) visualizing images (e.g., such as by showing multiple panes providing multiple image modes, such as, but not limited to, axial, coronal, sagittal, 3 dimensional (3D), etc.) (e.g., each image mode may represent a different aspect of an image (e.g., a CT DICOM image); showing at least one pane of an image; loading an image (e.g., a CT DICOM image) and displaying it on a computer for visualization purposes; allowing a user to interact with a displayed image in one or more panes by using the indicator element as described herein to visually move through the 3D data set and display the reformatted slices in the 3D view; etc.)) (see step S2 in FIG. 14); (iii) identifying a region of interest, which, for ablation, can be treating zone or target (e.g., a lesion or tumor) (see step S3 in FIG. 14); (iv) defining a target point, an insertion or entry point and a trajectory between the target and insertion points (see step S4 in FIG. 14) (as shown in step S4*b*, Step S4 may include repeating the process if there is one trajectory or there are multiple trajectories (and multiple target points) depending on a characteristic of a tumor or lesion); and (v) correspond the entry point in a particular image to an entry point for a body of the patient (see step S5 in FIG. 14).

Once the region of interest or target point and the insertion point are determined, the indictor element will display the location of these features within the three-dimensional image set. The clinician is then free to move through the three-dimensional image set by using the information provided in the indicator element to, for example: verify the accuracy of the location of these features on the images, determine if the margin is acceptable, view the trajectory (or trajectories), search the images for the location of other key features (e.g., blood vessels or bile ducts), or determine the number of needles and/or size of ablation therapy required.

Determination of the target points (and the number of target points) may be at the discretion of the clinicians in one or more embodiments, or may be dependent upon the characteristic(s) of the target biological object, such as a lesion or tumor (e.g., a size of the lesion or tumor, a shape of the lesion or tumor, etc.). The target point or points that is clinically the best choice (e.g., mathematically, statistically, etc.) may be selected via an algorithm for placement of the target point(s). In one or more embodiments, target point(s) may be determined by finding or determining a medial axis or center line of the target or treating zone (see step S4 of FIG. 14).

Figure 15:
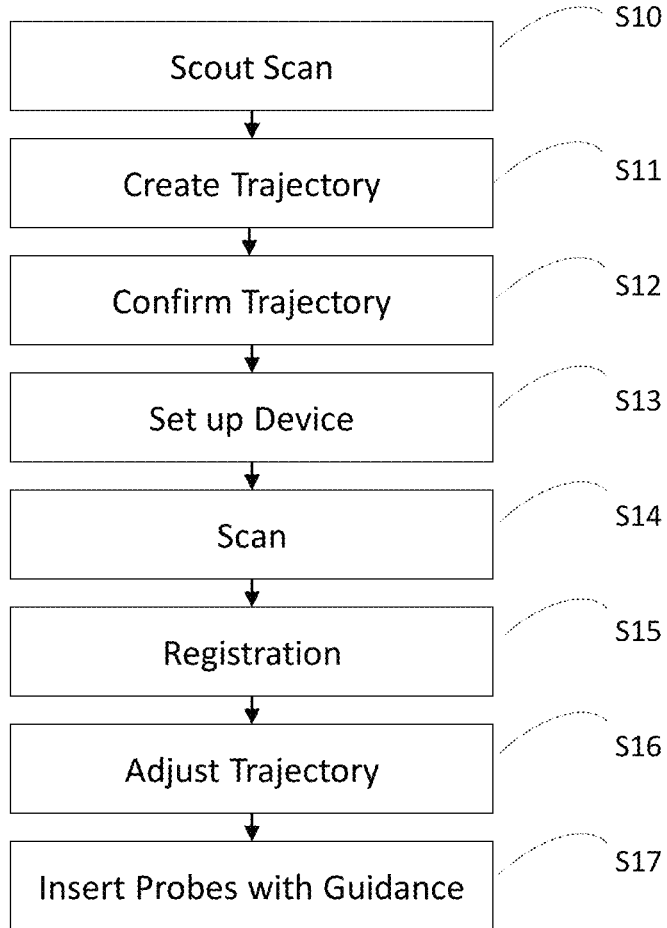
FIG. 15 is a flow chart showing at least one embodiment of a workflow for device placement and registration for performing ablation and/or needle guidance planning and/or performance in accordance with one or more aspects of the present disclosure.

In some embodiments, a device, such as the needle guide devices may be used in combination with systems described. Exemplary devices are described in U.S. Pat. Nos. 9,222,996 and 10,610,325, both of which are herein incorporated by reference in their entirety. Any suitable needle guide device may be used in conjunction with the embodiments of the present disclosure. In operation, as shown in FIG. 15, the user conducts a scout scan S10 because trajectory creation requires scanned images. The guidance application first visualizes scanned images and provides interface to create a trajectory S11. For example, the user uses a line extending between an insertion point and target point as a trajectory. The insertion point is on patient's skin and the target point is at or on a region of interest such as tumor. To confirm the trajectory (see step S12 of FIG. 15), the user may be provided multiple 2D images to aid the user readily visualize the trajectory as well as other potential other features of interest such as blood vessels other regions to be avoided by the needle. The guidance application may show image modes including Axial, Sagittal and/or Coronal views in this step S12. Users may confirm and modify trajectory on other image modes such as Trajectory view, Flythrough view and Arc view. The user can set up a device (see step S13 of FIG. 15) after they create a trajectory S11. In an exemplary embodiment, the user turns on a device and the guidance application electronically connects to it. Then, the guidance application is able to read status of the connected device. The user places the device on or near the planned insertion point on a patient. The user then conducts a CT scan with the device in place on the patient and the guidance application loads scanned images S14. For registration, the device may have fiducial markers which are visible in CT images and placed uniquely in 3D coordinates on the device, the guidance application is able to register the device in CT image(s) (see step S15 of FIG. 15). To complete this step, the user may confirm registration result. In one preferred embodiments, the confirmation occurs when the image mode Base view is displayed.

When using the guidance device as described in this embodiment, the insertion point is located at the center of the device. If the device is not fixed on a patient precisely such that the planned insertion point is located in the center of the device when placed on the patient, the guidance application can then adjust the trajectory based on the updated insertion point. The user may confirm and modify the adjusted trajectory and may do so in one (or more) of several different imagine modes, such as Arc view, Trajectory view, Flythrough view and/or other views. After the user fix the trajectory, the guidance application can, for example, calculate the angle of the needle trajectory and the insertion depth. Users rotates arc of the device, moves the needle holder and inserts the probe along the guidance S17.

Figures 16, 17:
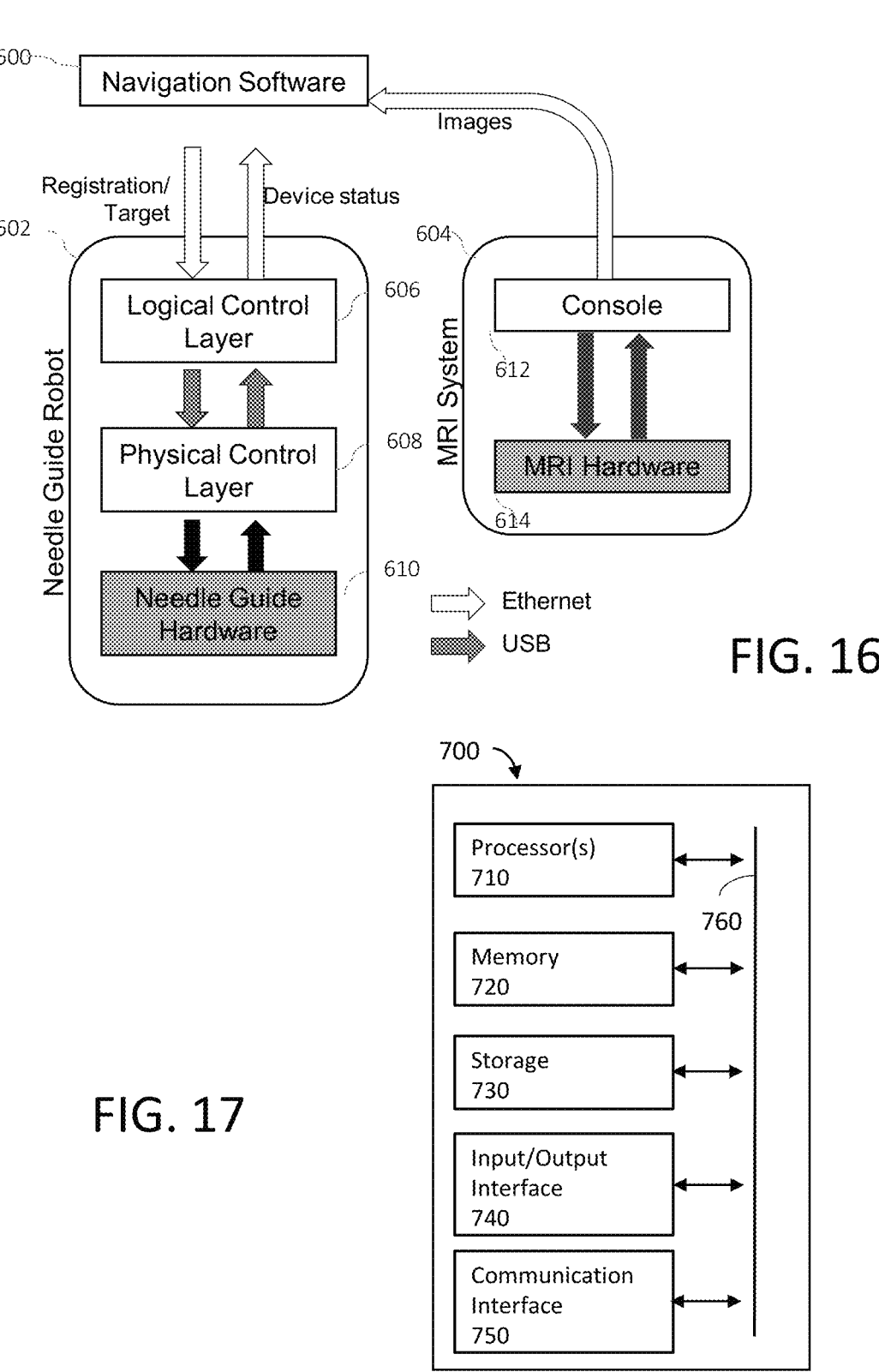
FIG. 16 illustrates an example system diagram for a needle guide device system including image software, robot control server of a needle guide device, and MRI system including an MRI scanner in accordance with some embodiments.
FIG. 17 illustrates an example computing system in accordance with some embodiments.

FIG. 16 illustrates an example system diagram for a needle guide device including imaging software, robot control server of a needle guide device, and MRI system including an MRI scanner in accordance with some embodiments. FIG. 16 represents one example of a system for a needle guide device, but the present disclosure is not limited to such a system. For example, according to some embodiments, the needle guide device is a manually operated device. The following description of FIG. 16 is merely an example of a needle guide system, which may be used in conjunction with the systems and methods described herein.

Robot Control Software

In some embodiments, a software system is provided that has three layers of components including, image guidance software 600, logical control layer 606, and physical control layer 608 (FIG. 16). Those components are implemented as independent software processes, and communicate with each other via, for example, Ethernet and Universal Serial Bus (USB). However, in other embodiments, two more of these components are integrated into a single software process.

The details of those three components are as follows:

Image Guidance Software

The image guidance software 600 is the top layer component in the system and is exemplified in FIG. 16. The image guidance software 600 works, for example, as a primary user interface for the physician and/or operator. It is implemented as described herein as a plug-in module for 3D Slicer, open-source medical image computing software and, through this or other software, receives images from the MRI System 604, which includes the console 612 and MRI hardware 614, which includes an MRI scanner. The image guidance software 600 assists the physician in performing the following tasks.

Needle placement planning. The physician can define a trajectory of needle placement by specifying the targets and skin entry point on the planning image. The software displays a section of the planning image along any plane and allows the physician to specify the points by, for example, clicking on it with a mouse. Once the trajectory has been defined, it can re-slice the 3D image with a plane along the trajectory so that the physician can find any critical structures and obstacles around the path (see FIG. 1). The defined trajectory is transferred to the robot control server 602. The final decision to move the actuator, however, may be made by the physician standing by the gantry; the actuators can be powered on when the physician presses down a footswitch.

Device-to-image registration. The software can automatically register the needle guide device to the image coordinate system. A registered device model is overlaid on the planning image data and its accessible range/reachable zone is presented on the image, so that the operator can confirm that the all targets are in range (see FIG. 1, item 103). Information is transferred to the robot control server 602 over the network using, for example, the OpenIGTLink protocol.

Monitoring and confirmation of probe placement. The software can be used to visualize the current position and orientation of the device with a 3D model overlaid on the images during planning for or performance of a procedure. In addition, it also can display confirmation images that show the probe inserted into the patient with the planned trajectory and target (see FIG. 1). Those features allow the physicians to monitor the device and confirm the probe placement.

Logical Control Layer

The Logical Control Layer (LCL) 606 sits in the middle layer of the system and interfaces the image guidance software 600 and low-level physical control layer (PCL) 608. This layer of the robot control server 602 can encapsulate the hardware and the kinematic structure of the device, and provide a device-independent application program interface (API) to the upper layer. Therefore, the LCL 606 consists of the following subcomponents:

TCP/IP network interface to the upper layer. Through this interface, the LCL 606 receives commands to the hardware from the upper layer including the target position, and provides the current status of the hardware (610) to the upper layer including the current position of the needle guide, and the status of the device. It also provides the required needle insertion depth as a result of kinematics computation (see Kinematics engine below) to the upper layer. In some embodiments, the network interface is compliant with the OpenIGTLink protocol, and thus it can communicate with software compatible with OpenIGTLink.

Kinematics engine. In some embodiments, the hardware-independent commands received from the upper layer are translated into the target positions of individual actuators based on the kinematics of the needle guide device, and sent to the PCL 608. Moreover, in some embodiments, current positions of individual actuators received from the PCL 608 are translated to the position and orientation of the needle guide and sent to the upper layer.

Serial interface to the lower layer. The LCL 606 communicates with the lower layer subcomponent through a universal serial bus (USB). Through this exemplary interface, target positions of individual actuators and other device-specific commands are sent to the PCL 608, while the current status of the device and the encoder readings of individual actuators are sent to the image guidance software 600. The information exchanged through this interface is dependent on the kinematic structure, but independent from the physical hardware (e.g. motor drivers and encoders).

Physical Control Layer

The role of the Physical Control Layer (PCL) 608 is to provide an interface that is independent from the physical input/output (I/O), but dependent on the kinematic structure. In some embodiments, the PCL 608 runs on a Linux-based embedded computer equipped with a USB interface for the communication with the LCL 606, and a digital input/output interface for reading inputs from encoders and footswitch and giving the target speeds of individual motors to the motor drivers. Once the controller receives target positions for individual actuators, it performs closed-loop PID control of individual motors. Throughout this process, the PCL 608 can optionally keep sending current positions and other device status.

Computing System

FIG. 17 provides a computing system for the device and software as described herein. In some embodiments, the computing system 700 includes the image guidance software described herein. For example, in some embodiments, the computing system 700 may include the image guidance software 600 of FIG. 13, components of which are described in detail herein. The various programs and data—for example, software modules, libraries, tools, user interface elements, or other components—of the image guidance software reside in the computing system 700 in any suitable manner, in accordance with various embodiments. For example, these components may reside in one or multiple storage locations. The components of the image guidance software may be provided as part(s) of a single software application or as a plurality of stand-alone software applications. The computing system 700 provides access to the image guidance software. In some embodiments, the image guidance software executing on the computing system 700 performs one or more steps of one or more methods described or illustrated herein, or provides functionality described or illustrated herein. For example, programs of the image guidance software may include instructions that, when executed by one or more processors, cause the computing system 700 to perform the process described herein.

The term computing system as used herein includes but is not limited to one or more software modules, one or more hardware modules, one or more firmware modules, or combinations thereof, that work together to perform operations on electronic data. The physical layout of the modules may vary. A computing system may include multiple computing devices coupled via a network. A computing system may include a single computing device where internal modules (such as a memory and processor) work together to perform operations on electronic data. In some embodiments, a single computing system 700 includes the image guidance software.

In some embodiments, the image guidance software executing on the computing system 700 interacts with the robot control server 602 and with the MRI System 604. The computing system 700 may use any suitable protocol(s), standard(s), data exchange format(s), or combination(s) of these, to communicate with and send/receive information to/from one or more of the systems described herein. The computing system 700 may send and receive information and requests using OpenIGTLink. The computing system 700 can receive, send, and store DICOM (Digital Imaging and Communications in Medicine) files and data. For example, the computing system 700 may receive a medical image from the MRI System 604. Additionally, the computing system 700 may send HTTP requests and provide HTTP responses. The responses may include Hyper Text Markup Language (HTML) files, or other suitable files, executable code, such as JAVASCRIPT, form elements, images, or other content. One or more elements of the content may be stored at the computing system 700. In some embodiments, the computing system 700 uses Simple Object Access Protocol (SOAP) to receive and send messages.

The computing system 700 as shown in FIG. 17 includes one or more processor(s) 710, memory 720, storage 730, an input/output (I/O) interface 740, a communication interface 750, and a bus 760. The computing system 700 may take any suitable physical form. For example, and not by way of limitation, the computing system 700 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, PDA, a tablet computer system, one or more servers, a workstation, or a combination of two or more of these. In some embodiments, the computing system 700 is unitary. In some embodiments, the computing system 700 is distributed. The computing system 700 may span multiple locations. The computing system 700 may span multiple machines.

The processor(s) 710 include hardware for executing instructions, such as those making up a computer program. The processor(s) 710 may retrieve the instructions from the memory 720, the storage 730, an internal register, or an internal cache. The processor(s) 710 then decode and execute the instructions. Then, the processor(s) 710 write one or more results to the memory 720, the storage 730, the internal register, or the internal cache. The processor(s) 710 may provide the processing capability to execute the operating system, programs, user and application interfaces, and any other functions of the computing system 700.

The processor(s) 710 may include a central processing unit (CPU), one or more general-purpose microprocessor(s), application-specific microprocessor(s), and/or special purpose microprocessor(s), or some combination of such processing components. The processor(s) 710 may include one or more graphics processors, video processors, audio processors and/or related chip sets.

In some embodiments, the memory 720 includes main memory for storing instructions for the processor(s) 710 to execute or data for the processor(s) 710 to operate on. By way of example, the computing system 700 may load instructions from the storage 730 or another source to the memory 720. During or after execution of the instructions, the processor(s) 710 may write one or more results (which may be intermediate or final results) to the memory 720. One or more memory buses (which may each include an address bus and a data bus) may couple the processor(s) 710 to the memory 720. One or more memory management units (MMUs) may reside between the processor(s) 710 and the memory 720 and facilitate accesses to the memory 720 requested by the processor(s) 710710. The memory 720 may include one or more memories. The memory 502 may be random access memory (RAM).

The storage 730 stores data and/or instructions. As an example and not by way of limitation, the storage 730 may include a hard disk drive, a floppy disk drive, flash memory, an optical disc, a magneto-optical disc, magnetic tape, or a Universal Serial Bus (USB) drive or a combination of two or more of these. In some embodiments, the storage 730 is a removable medium. In some embodiments, the storage 730 is a fixed medium. In some embodiments, the storage 730 is internal to the computing system 700. In some embodiments, the storage 730 is external to the computing system 700. In some embodiments, the storage 730 is non-volatile, solid-state memory. In some embodiments, the storage 730 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. The storage 730 may include one or more memory devices. The storage 730 may store application data, program modules and other information. One or more program modules stored in the storage 730 are configured to cause various operations and processes described herein to be executed. In some embodiments, the image guidance software resides on the storage 730 and executes on the computing system 700. The storage 730 may further store other programs and/or drivers that enable various functions of the computing system 700, graphical user interface (GUI) functions, and/or processor functions. The storage 730 may also store data files including, for example, image data, user data, configuration information, GUI components, such as graphical elements or templates, or other data required by the computing system 700.

The I/O interface 740 includes hardware, software, or both providing one or more interfaces for communication between the computing system 700 and one or more I/O devices. In some embodiments, the computing system 700 includes one or more I/O devices. One or more of these I/O devices may enable communication between a person and the computing system 700. On I/O device is the input device for scrolling along the indicator element. By way of example and not by way of limitation, an I/O device may include a keyboard, keypad, microphone, monitor, mouse, touchpad, speaker, still camera, stylus, tablet, touch screen, trackball, video camera, another suitable I/O device or a combination of two or more of these. An I/O device may include one or more sensors. In some embodiments, the I/O interface 740 includes one or more device or software drivers enabling the processor(s) 710 to drive one or more of these I/O devices. The I/O interface 740 may include one or more I/O interfaces.

In some embodiments, the computing system 700 includes a display. For example, the display may be a liquid crystal display (LCD). In some embodiments, the image guidance software running on the computing system 700 presents GUI data on the display. In some embodiments, the GUI data is presented in conjunction with medical image data. Regarding outputting signals to the display, the processor(s) 710 rasterize an image to be displayed on the display, and transfer the rasterized image to the display via the I/O interface 740. The display then displays the image, such as a GUI. The processor(s) 710 are further operable to cause other types of images, such as medical images from the MRI System 604, to be displayed on the display. The computing system 700 may receive an input signal based on user inputs at the display. For example, in some embodiments, the display includes a touch sensitive element operable to receive user inputs or commands based on the touching one or more interface elements on the display. The interface element may be a graphical object presented on the display. A user may touch the touch sensitive display with a finger, stylus, or other tool to provide a user input. When the user touches a specific region on the touch sensitive display, the processor(s) 710 are notified via the I/O interface 740 of the coordinates of the region. The processor(s) 710 determine the content of a user input based on the notified coordinates and the display contents on the display, and execute processing based on them. In some embodiments, a mouse or touchpad is used in conjunction with information presented on the display to receive user inputs and selections. For example, a cursor may be used to select one or more interface elements presented in the GUI on the display. According to various embodiments, the touch sensitive display, the cursor, or other suitable method for providing an input, is used to specify one or more location(s) on a medical image presented in the GUI on the display to indicate, for example, a target and a planned insertion point for inserting a needle into a patient.

In some embodiments, the computing system 700 includes a keyboard/keypad. User inputs may also be provided via the keyboard/keypad. When the user presses a hard key of the keyboard/keypad, the processor(s) 710 are notified via the I/O interface 740 of information indicative of the user input. The processor(s) 710 execute processing based on the notification. The hard keys and/or buttons of the keyboard/keypad may be arranged in any suitable configuration. Furthermore, the input structures may include buttons, keys, switches, control pads, or other suitable structure, depending on specific implementation requirements.

The communication interface 750 includes hardware, software, or both providing one or more interfaces for communication (such as, for example, packet-based communication) between the computing system 700 and one or more other computing systems or one or more networks. As an example and not by way of limitation, the communication interface 505 may include a network interface card (NIC) or a network controller for communicating with an Ethernet or other wire-based network or a wireless NIC (WNIC) or wireless adapter for communicating with a wireless network, such as a WI-FI network. This disclosure contemplates any suitable network and any suitable communication interface 750 for it. As an example and not by way of limitation, the computing system 700 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, the computing system 700 may communicate with a wireless PAN (WPAN) (such as, for example, a Bluetooth WPAN or an ultra-wideband (UWB) network), a WI-FI network, a WI-MAX network, a cellular telephone network (such as, for example, a Global System for Mobile Communications (GSM) network), or other suitable wireless network or a combination of two or more of these. The computing system 700 may include any suitable communication interface 750 for any of these networks, where appropriate. The communication interface 505 may include one or more communication interfaces 750.

The bus 760 interconnects various components of the computing system 700 thereby enabling the transmission of data and execution of various processes. The bus 760 may include one or more types of bus structures including a memory bus or memory controller, a peripheral bus, and a local bus using any of a variety of bus architectures.

The above description serves to explain principles of the present disclosure; but the present disclosure should not be limited to the examples described above. For example, the order and/or timing of some of the various operations may vary from the examples given above without departing from the scope of the present disclosure. Further, by way of example, the type of network and/or computing systems may vary from the examples given above without departing from the scope of the present disclosure. Other variations from the examples given above may also exist without departing from the scope of the present disclosure. While particular examples of GUIs are illustrated, it will be understood that various other implementations of GUIs are within the scope of the present disclosure. For example, various features of the illustrated examples could be modified, rearranged, or removed, or one or more features could be added without departing from the scope of the present disclosure.

The scope of the present disclosure includes a computer-readable medium storing instructions that, when executed by one or more processors, cause the one or more processors to perform one or more embodiments described herein. Examples of a computer-readable medium include a hard disk, a floppy disk, a magneto-optical disk (MO), a compact-disk read-only memory (CD-ROM), a compact disk record-able (CD-R), a CD-Rewritable (CD-RW), a digital versatile disk ROM (DVD-ROM), a DVD-RAM, a DVD-RW, a DVD+RW, magnetic tape, a nonvolatile memory card, and a ROM. Computer-executable instructions can also be sup-plied to the computer-readable storage medium by being downloaded via a network.

While the present disclosure has been described with reference to exemplary embodiments, it is to be understood that the present disclosure is not limited to the exemplary embodiments described.

Although the disclosure herein has been described with reference to particular embodiments, it is to be understood that these embodiments are merely illustrative of the prin-ciples and applications of the present disclosure (and are not limited thereto). It is therefore to be understood that numer-ous modifications may be made to the illustrative embodi-ments and that other arrangements may be devised without departing from the spirit and scope of the present disclosure. The scope of the following claims is to be accorded the broadest interpretation so as to encompass all such modifi-cations and equivalent structures and functions.

The invention claimed is:

1. An image processing apparatus comprising a processor that operates to:
   acquire a three-dimensional image set comprising a stack of image slices;
   cause a display to display a first image slice from the three-dimensional image set in a first image mode;
   cause the display to display, concurrent with the first image slice, a first indicator element associated with the first image mode;
   cause a display to display a second image slice from the three-dimensional image set in a second image mode;
   cause the display to display, concurrent with the first image slice, a second indicator element associated with the second image mode;
   wherein the first indicator element indicates:
      a location of the first image slice within the three-dimensional image set, with a first marker; and
      a location of the at least one region of interest and/or at least one target point with a third marker;
   wherein the second indicator element indicates a location of the second image slice within the three-dimensional image set with a second marker; and
   wherein, in response to receiving a user input for selecting a visualized image slice within the second indicator element associated with the second image mode, the processing apparatus is adapted to:
      cause the display displaying the second image slice in the second image mode to change the displayed second image slice to an updated second image slice that corresponds to a location intersecting with the displayed first image slice, and
      cause the display displaying the first image slice in the first image mode to change the displayed first image slice to an updated first image slice that corresponds to the visualized image slice within the second indicator element.

2. The image processing apparatus of claim 1, wherein at least one of the first and second image modes is an imaging mode that is out-of-plane compared to the three-dimensional image set.

3. The image processing apparatus of claim 1, wherein the first and second image mode are selected from: an axial image mode, a sagittal image mode, a coronal image mode, an arc image mode, a trajectory image mode, a base image mode, and a flythrough image mode.

4. The image processing apparatus of claim 1, wherein the first indicator element indicates a relative location of the second image slice as related to the first image slice.

5. The image processing apparatus of claim 1, wherein, in response to receiving a user input for selecting an image slice within the indicator element associated with the first image mode, the processing apparatus is adapted to:
   cause the display displaying the first image slice in the first image mode to change the displayed first image slice to an updated first image slice that corresponds to selected slice within the first indicator element, and
   cause the display displaying the second image slice in the second image mode to change the displayed second image slice to an updated second image slice that corresponds to a location intersecting with the dis-played first image slice.

6. The image processing apparatus of claim 5, wherein the processor is adapted to:
   cause the display to display a third image slice from the three-dimensional image set in a third image mode;

cause the display to display, concurrent with the third image slice, a third indicator element associated with the third image mode;

cause the display displaying the third image slide in the third image mode to change the displayed third image slice to an updated third image slice that corresponds to a location intersecting with the displayed first or second image slice.

7. The image processing apparatus of claim 1, wherein the processor generates and displays at least one of:

a reference trajectory connecting the target point and an insertion point, a reachable zone, and one or more fiducial markers.

8. The image processing apparatus of claim 1, wherein the at least one region of interest or at least one target point in the image and the at least one insertion point are determined in response to receiving a user input for selecting a position in a displayed image slice.

9. The image processing apparatus of claim 1, wherein the processor displays the region of interest and an insertion point, superimposed on at least one of the first or second image slice.

10. The image processing apparatus of claim 1, further comprising an input means for inputting a desired viewing location within the three dimensional data set.

11. A method of performing planning or treatment for a percutaneous probe treatment, comprising:

acquiring a three-dimensional image set comprising a stack of image slices;

causing a display to display a first image slice from the three-dimensional image set in a first image mode;

causing the display to display, concurrent with the first image slice, a first indicator element associated with the first image mode;

causing a display to display a second image slice from the three-dimensional image set in a second image mode;

causing the display to display, concurrent with the first image slice, a second indicator element associated with the second image mode;

wherein the second indicator element indicates:

a location of the first image slice within the three-dimensional image set, with a first marker; and a location of the at least one region of interest and/or at least one target point with a third marker;

wherein the second indicator element indicates a location of the second image slice within the three-dimensional image set with a second marker; and wherein, in response to receiving a user input for selecting a visualized image slice within the second indicator element associated with the second image mode, the processing apparatus is adapted to:

cause the display displaying the second image slice in the second image mode to change the displayed second image slice to an updated second image slice that corresponds to a location intersecting with the displayed first image slice, and cause the display displaying the first image slice in the first image mode to change the displayed first image slice to an updated first image slice that corresponds to the visualized image slice within the second indicator element.

12. The method of claim 11, further comprising causing the processor to display, on the image slice, when applicable, at least one of:

a reference trajectory connecting the target point and an insertion point, a reachable zone, and one or more fiducial markers.

13. The method of claim 11, further comprising receiving at least one user input to acquire the location of at least one region of interest or at least one target point in the image and the at least one insertion point.

14. An image processing apparatus comprising a processor that operates to:

acquire a three-dimensional image set comprising a stack of image slices;

cause a display to display:

(a) a first image slice from the three-dimensional image set in a first image mode and a first indicator element associated with the first image mode and containing a first marker that indicates a location of at least one of the first image slice within the three-dimensional image set and a third marker that indicates an insertion point, a target point, or a region of interest; and (b) a second image slice from the three-dimensional image set in a second image mode and a second indicator element associated with the second image mode and containing a second marker that indicates at least one of a location of the second image slice within the three-dimensional image set, and a fourth marker that indicates an insertion point, a target point, or a region of interest;

wherein the processor further operates, based on a user selecting and moving the first marker or the second marker, to:

(a) update the display of the first image slice to an updated first image slice in the first image mode, wherein the first marker indicates a location of the updated first image slice and the third marker indicates the insertion point, the target point, or the region of interest; and (b) update the display of the second image slice to an updated second image slice in the second image mode, wherein the second marker indicates a location of the updated second image slice and the fourth marker indicates the insertion point, the target point, or the region of interest.

15. The image processing apparatus of claim 14, wherein at least one of the first and second image modes is an imaging mode that is out-of-plane compared to the three-dimensional image set.

16. The image processing apparatus of claim 14, wherein the first and second image mode are selected from: an axial image mode, a sagittal image mode, a coronal image mode, an arc image mode, a trajectory image mode, a base image mode, and a flythrough image mode.

17. The image processing apparatus of claim 14, wherein the processor is adapted to:

cause the display to display (c) a third image slice from the three-dimensional image set in a third image mode; and wherein the processor further operates, based on a user selecting and moving the first marker or the second marker, to:

(c) update the display of the third image slice to an updated third image slice in the third image mode.

18. The image processing apparatus of claim 14, wherein the processor generates and displays at least one of:

a reference trajectory connecting the target point and the insertion point, a reachable zone, and one or more fiducial markers, on at least the first indicator element and the second indicator element.

19. A method of performing planning or treatment for a percutaneous probe treatment, comprising:

acquiring, by a processor, a three-dimensional image set comprising a stack of image slices;

causing a display to display:

(a) a first image slice from the three-dimensional image set in a first image mode and a first indicator element associated with the first image mode and containing a first marker that indicates a location of at least one of the first image slice within the three-dimensional image set, and a third marker that indicates an insertion point, a target point, or a region of interest; and (b) a second image slice from the three-dimensional image set in a second image mode and a second indicator element associated with the second image mode and containing a second marker that indicates at least one of a location of the second image slice within the three-dimensional image set, an insertion point, a target point, or a region of interest;

wherein the processor further operates, based on a user selecting and moving the first marker or the second marker, to:

(a) update the display of the first image slice to an updated first image slice in the first image mode, wherein the first marker indicates a location of the updated first image slice, and the third marker indicates the insertion point, the target point, or the region of interest; and (b) update the display of the second image slice to an updated second image slice in the second image mode, wherein the second marker indicates a location of the updated second image slice, the insertion point, the target point, or the region of interest.

20. A imaging server storing an imaging application having instructions that, when executed by the processor, cause an ablation server to perform the method according to claim 19.

21. A non-transitory computer-readable storage medium storing an imaging application to cause an ablation server to perform the method according to claim 19.

\* \* \* \* \*